(12) United States Patent
Hareyama et al.

(10) Patent No.: US 6,306,131 B1
(45) Date of Patent: Oct. 23, 2001

(54) ELECTRIC MEDICAL APPARATUS

(75) Inventors: Norihiko Hareyama; Kouji Yamauchi; Shinji Hatta; Naomi Sekino, all of Hachioji (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/388,783

(22) Filed: Sep. 2, 1999

(30) Foreign Application Priority Data

Sep. 30, 1998 (JP) .................................................. 10-278900

(51) Int. Cl.[7] .................................................. A61B 18/18
(52) U.S. Cl. .................................. 606/38; 606/37; 606/42
(58) Field of Search .................................. 606/32, 34, 35, 606/37, 41, 42

(56) References Cited

U.S. PATENT DOCUMENTS

| | | |
|---|---|---|
| 5,269,780 | 12/1993 | Roos . |
| 5,334,193 * | 8/1994 | Nardella et al. .......................... 606/41 |
| 5,496,312 * | 3/1996 | Klicek ...................................... 606/34 |
| 5,556,396 * | 9/1996 | Cohen et al. ............................. 606/42 |
| 5,558,671 | 9/1996 | Yates . |
| 5,817,093 * | 10/1998 | Williamson, IV et al. ............. 606/50 |
| 5,836,943 * | 11/1998 | Miller, III ................................ 606/34 |

* cited by examiner

*Primary Examiner*—Michael Peffley
(74) *Attorney, Agent, or Firm*—Frishauf, Holtz, Goodman, Langer & Chick, P.C.

(57) ABSTRACT

An electric medical apparatus according to the present invention performs an incising treatment automatically after the coagulating treatment has been performed without a necessity for an operator to perform another operation between the two treatment operations when the incising treatment performs after a coagulating treatment. The electric medical apparatus comprises a CPU, a waveform generating circuit, an amplifier and an output control unit to supply an output for performing the coagulating treatment to a treatment device and an output for performing the incising treatment to the treatment device. The impedance of a living tissue with which the treatment device is brought into contact is measured and calculated by a voltage sensor, a current sensor and an impedance calculating portion. In accordance with a result of the calculation performed by the impedance calculating portion, an output from an electric knife body is, by the CPU, switched to the output for the incising treatment after the coagulating treatment has been performed.

5 Claims, 30 Drawing Sheets

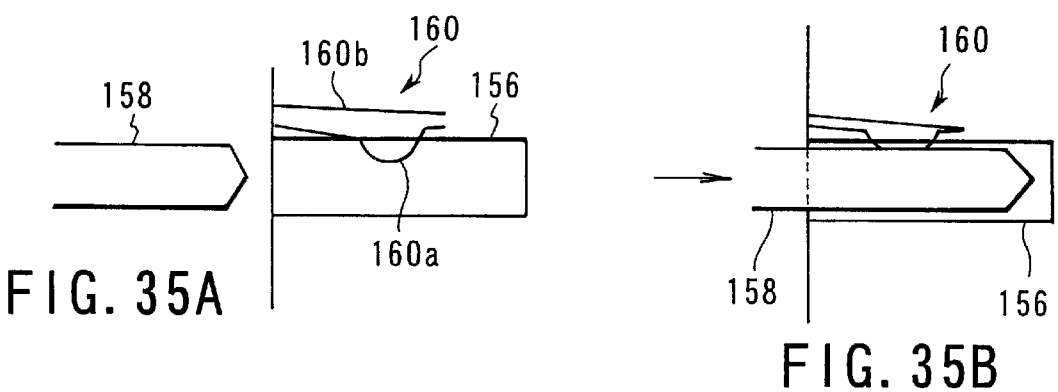
FIG. 35A
FIG. 35B
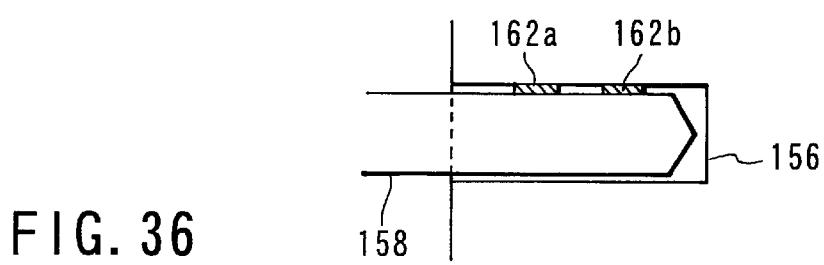
FIG. 36
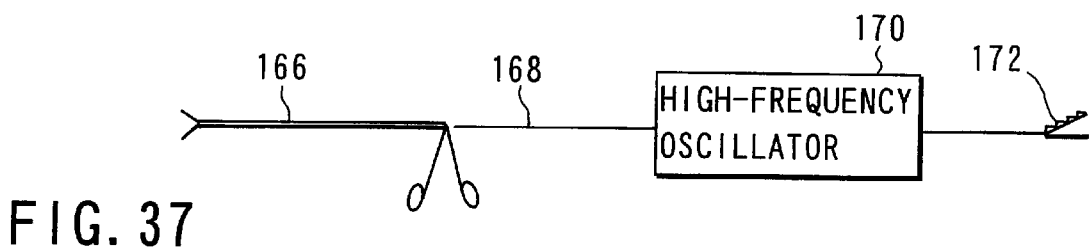
FIG. 37
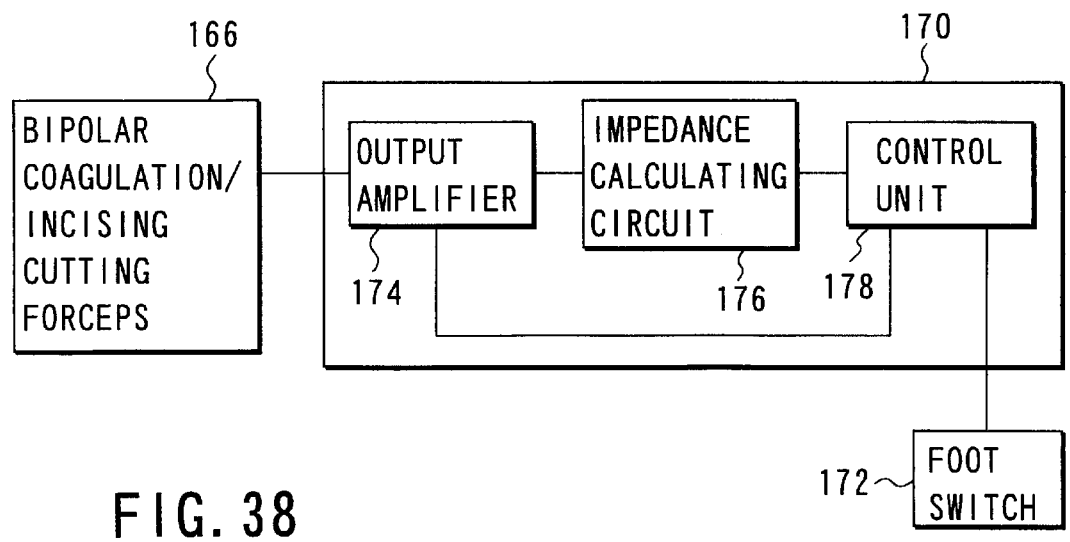
FIG. 38

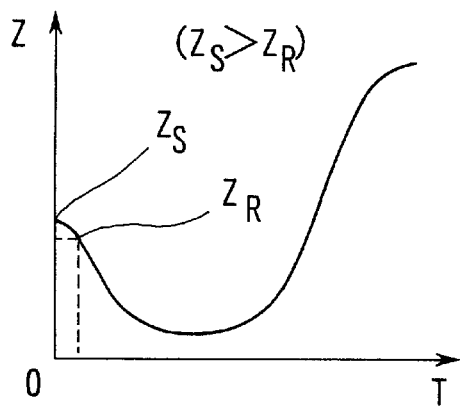 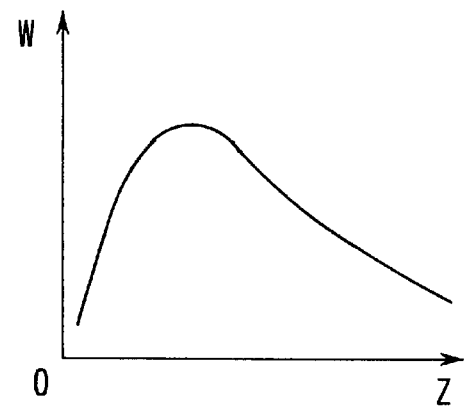
FIG. 40A    FIG. 40B
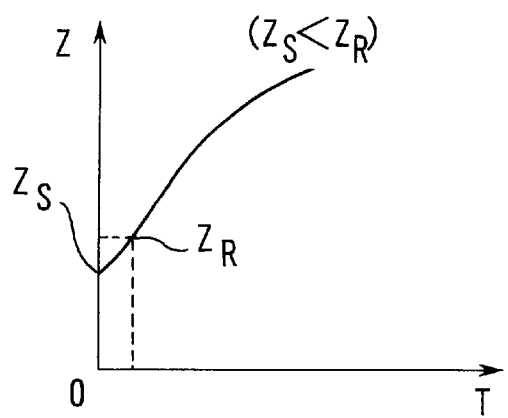 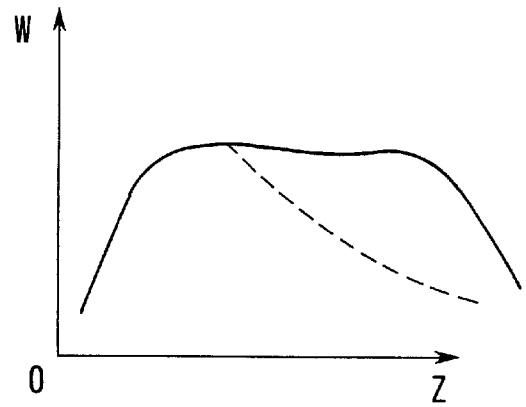
FIG. 41A    FIG. 41B

ELECTRIC MEDICAL APPARATUS

BACKGROUND OF THE INVENTION

The present invention relates to an electric medical apparatus, and more particularly to an electric medical apparatus which supplies a high-frequency electric current to a living tissue to use heat generated by the high-frequency electric current so as to treat the living tissue such that the mode is switched between, for example, incision and coagulation.

The electric medical apparatus supplies a high-frequency electric current to a living tissue to perform an incising treatment or a coagulating treatment or the like. The apparatus has been employed in a usual surgical operation. An apparatus is known among the electric medical apparatuses of a type which measures the impedance of a living tissue to control the output of the apparatus in accordance with a result of the measurement.

A technique has been disclosed in U.S. Pat. No. 5,558,671 which measures a minimum value of the impedance of the organism to use a function of the minimum impedance to determine the impedance at a moment of time at which the coagulation of the organism is completed. In accordance with a load curve of the system, a control unit causes optimum electric power to be output. Thus, the coagulation operation of the electric medical apparatus can satisfactorily be performed.

If the output for performing the incising operation is first used to excise the living tissue which is performed by the electric medical apparatus, coagulation cannot sufficiently be completed to prevent bleeding.

The technique disclosed in U.S. Pat. No. 5,558,671 enables an operator to perform another operation only when the operator switches the output switch to perform another operation after the coagulating treatment has automatically be completed. When an incising treatment is performed after the coagulating operation, the operator must perform the other burdensome operation.

A triple-pole probe serving as a forceps, which is capable of performing coagulating and incising operations, has been disclosed in U.S. Pat. No. 5,269,780. The foregoing triple-pole probe must, however, perform a complicated operation because a selection switch provided for the probe must be operated to switch the electrode.

BRIEF SUMMARY OF THE INVENTION

Accordingly, an object of the present invention is to provide an electric medical apparatus which is capable of automatically performing an incising treatment after a coagulating treatment has been performed without a necessity for an operator to perform another operation when the incising treatment is performed after the coagulating operation has been completed.

According to one aspect of the present invention, there is provided an electric medical apparatus having a treatment device which is brought into contact with a living tissue and which is supplied with high-frequency electric power from a high-frequency power supply unit so as to coagulate or excise the living tissue, the electric medical apparatus comprising: coagulation output means for supplying an output for performing the coagulating treatment to the treatment device; incision output means for supplying an output for performing the incising treatment to the treatment device; and control means for switching the output from the high-frequency power supply unit to the incision output which is supplied by the incision output means after the coagulating treatment has been performed by the coagulation output means.

According to another aspect of the present invention, there is provided an electric medical apparatus having a treatment device which is brought into contact with a living tissue and which is supplied with high-frequency electric power from a high-frequency power supply unit so as to coagulate or excise the living tissue, the electric medical apparatus comprising: coagulation output means for supplying an output for performing the coagulating treatment to the treatment device; incision output means for supplying an output for performing the incising treatment to the treatment device; and control means for switching the output from the high-frequency power supply unit from the coagulation output means to the incision output means in accordance with at least either or a rate of change in the impedance of the living tissue and the impedance.

According to another aspect of the present invention, there is provided an electric medical apparatus having a treatment device which is brought into contact with a living tissue and which is supplied with high-frequency electric power from a high-frequency power supply unit so as to coagulate or excise the living tissue, the electric medical apparatus comprising: coagulation output means for supplying an output for performing the coagulating treatment to the treatment device; incision output means for supplying an output for performing the incising treatment to the treatment device; and control means for switching the output to the output for performing the incising treatment from the incision output means after the coagulating treatment has been completed by the coagulation output means and causing standby to be put.

According to another aspect of the present invention, there is provided an electric medical apparatus having a treatment device which is brought into contact with a living tissue and which is supplied with high-frequency electric power from a high-frequency power supply unit so as to coagulate or excise the living tissue, the electric medical apparatus comprising: measuring means for measuring the impedance of the living tissue; and control means for detecting a point of change when at least either of a rate of change in the impedance or the impedance is larger than a predetermined value or a constant-value multiple of a minimum value of the impedance to control at least any one of change in an output waveform, change in a load characteristic and output voltage.

According to another aspect of the present invention, there is provided an electric medical apparatus having a treatment device which is brought into contact with a living tissue and which is supplied with high-frequency electric power from a high-frequency power supply unit so as to coagulate or excise the living tissue, the electric medical apparatus comprising: measuring means for measuring the impedance of the living tissue; and control means for detecting a point of change when at least either of a rate of change in the impedance or the impedance is larger than a predetermined value or a constant-value multiple of a minimum value of the impedance to reduce the output and control at least any one of change in an output waveform, change in a load characteristic and output voltage when a signal has been received afterwards.

According to another aspect of the present invention, there is provided an electric medical apparatus having a treatment device which is brought into contact with a living tissue and which is supplied with high-frequency electric power from a high-frequency power supply unit so as to coagulate or excise the living tissue, the electric medical apparatus comprising: forceps recognizing means to which a forceps having three or more electrodes can be connected and which is capable of recognizing a connected forceps is the forceps having three or more electrodes; measuring means for measuring the impedance of the living tissue; and control means for detecting a point of change in accordance with an impedance detected by the measuring means, switching an output for performing a coagulating treatment to an output for performing an incising treatment when the point of change has been detected and switching the electrodes from which output is made from a combination of electrodes for the coagulating treatment to a combination of electrodes for the incising treatment.

According to another aspect of the present invention, there is provided a high-frequency oscillator incorporating means for calculating impedance from output current and voltage when a high-frequency output is performed, the high-frequency oscillator comprising: control means for comparing an initial impedance detected when an output for a coagulating treatment is performed with impedance which is calculated afterwards to control a load characteristic during output.

According to another aspect of the present invention, there is provided a high-frequency oscillator which is capable of supplying outputs for a coagulating treatment and incising treatment to a high-frequency treatment device having a water supply function to coagulate/excises a living tissue, wherein a water-supply valve is automatically opened after input to perform an output for the incising treatment, and then the water-supply valve is closed.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 20A and 20B show a fourteenth embodiment of the present invention, in which FIG. 20A is a diagram showing an example of an electric medical apparatus according to the fourteenth embodiment and FIG. 20B is an enlarged cross sectional view showing a portion of a holding portion of the bipolar cutting forceps shown in FIG. 20A;

FIGS. 35A and 35B are diagrams showing an example of a three-electrode detection portion according to eighteenth to twenty-first embodiment, in which FIG. 35A is a diagram showing a state in which a detection switch 160 is not conducted and FIG. 35B is a diagram showing a state in which the detection switch 160 is conducted;

FIG. 36 is a diagram showing a twenty-second embodiment of the present invention such that a three-electrode detection portion is illustrated;

FIG. 37 is a diagram showing the schematic structure of an electric medical apparatus according to a twenty-third embodiment of the present invention;

FIG. 38 is a block diagram showing the electrical structure of the electric medical apparatus shown in FIG. 37;

FIGS. 40A and 40B are graphs showing a usual coagulation output performed in step S266 in the flow chart shown in FIG. 39, in which FIG. 40A is a graph showing change in the impedance and FIG. 40B is a graph showing a load characteristic;

FIGS. 41A and 41B are graphs showing a characteristic in a coagulation mode in which the output is not reduced even with a high impedance value in step S267 in the flow chart shown in FIG. 39, in which FIG. 41A is a graph showing change in the impedance and FIG. 41B is a graph showing a load;

DETAILED DESCRIPTION OF THE INVENTION

Figure 1:
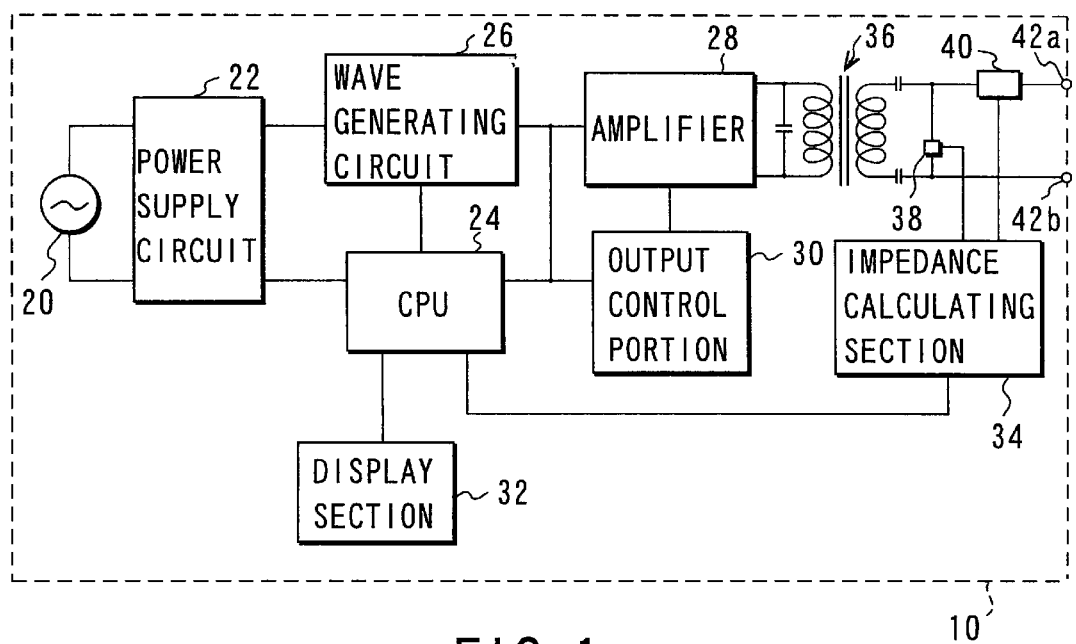
FIG. 1 is a diagram showing en electrical structure of an electric knife body of an electric medical apparatus according to a first embodiment of the present invention.

Referring to the drawings, embodiments of the present invention will now be described.

Referring to FIGS. 1 to 4, a first embodiment of the present invention will now be described.

Figure 2:
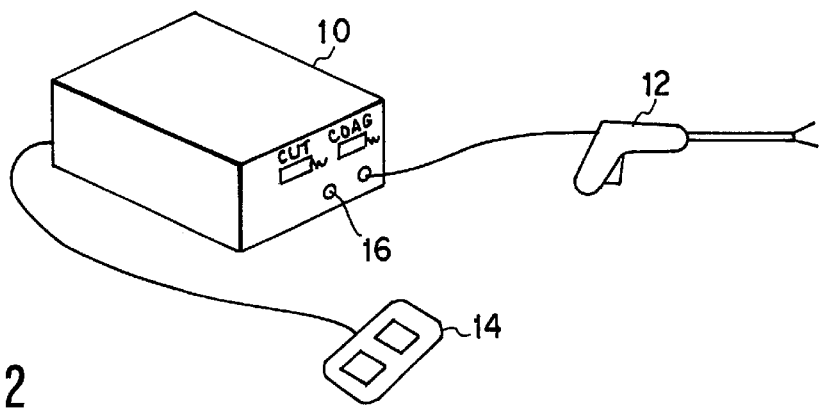
FIG. 2 is a diagram showing the schematic structure of the electric medical apparatus according to the first embodiment of the present invention.

FIG. 2 is a diagram showing the schematic structure of an electric medical apparatus according to the first embodiment of the present invention.

Referring to FIG. 2, the electric medical apparatus according to the present invention incorporates an electric knife body 10; a bipolar cutting forceps 12 connected to the electric knife body 10 through a cable to perform a treatment of a portion of a patient; and a foot switch 14 arranged to switch a variety of operations and provided with an output switch. The electric knife body 10 has a panel provided with a mode selection switch 16 for selecting a mode between a normal mode and an automatic coagulation/incision mode.

FIG. 1 is a block diagram showing an electrical structure of the electric knife body 10.

Referring to FIG. 1, a power supply circuit 22 connected to a commercial power source 20 is connected to a CPU 24 which is a control unit which controls the total operation of the electric knife body 10. The CPU includes an opening detection portion and a triple-electrode determining portion. The power supply circuit 22 is also connected a wave generating circuit 26 for generating waves having waveforms corresponding to coagulation and incision. An amplifier 28 for amplifying the generated wave and an output control unit 30, which has a voltage-limiter setting portion for controlling a load characteristic of the output and a switch operating portion, are connected to the CPU 24 and the wave generating circuit 26.

Moreover, a display portion 32, which has an LED portion and a loud speaker unit for indicating information, and an impedance calculating portion 34, which calculates the impedance of a load through the bipolar cutting forceps 12, are connected to the CPU 24.

A voltage sensor 38 and a current sensor 40 connected to the impedance calculating portion 34 are connected to the amplifier 28 through an output transformer 36. Note that reference numerals 42a and 42b represent terminals for connecting the bipolar cutting forceps 12.

Referring to a flow chart shown in FIG. 4, the operation of the electric medical apparatus according to the first embodiment of the present invention will now be described.

When a normal mode-selection is performed, either of output switches (not shown) corresponding to coagulation and incision is depressed to perform a required output. When an automatic coagulation/incision mode selection is performed, the following operation is performed when the incision switch has been depressed.

When the foot switch 14 or a hand switch (not shown) is switched on in step S1, output is started in step S2 such that output electric power (Pout) satisfies P1=40 W and a voltage limiter level (Vlim) satisfies Vlim=60V. At this time, output sound 1 is produced. The foregoing output has an output load characteristic suitable to coagulating the organism.

In step S3 the state of the output switch is determined. When the switch has been switched on, the operation proceeds to step S4. Thus, measured values are acquired from the voltage sensor 38 and the current sensor 40 by the impedance calculating portion 34 so that impedance Z and impedance change rate dZ are calculated.

In step S5 the value of the calculated impedance Z is compared with a predetermined minimum value Zmin. If the calculated impedance Z is the minimum value, the operation proceeds to step S6 so that the value is stored as Zmin. If impedance Z is larger than the minimum value Zmin, the operation proceeds to step S7.

In step S7 whether or not the impedance change rate dZ is larger than a predetermined value dZ1=+300 Ω/sec is determined by a comparing operation. If dZ≧dZ1, the operation proceeds to step S8 so that the voltage limiter level Vlim is set such that Vlim2=200V. Simultaneously, output sound 2 is produced. The foregoing output has an output load characteristic suitable to the incising operation. Then, the incising operation is started.

If dZ≧dZ1 is not satisfied in step S7 or if step S8 has been completed, the operation is returned to step S3.

If a determination is made at arbitrary moment of time in step S3 that the switch has been switched off, the operation proceeds to step S9. Thus, output is interrupted.

Figure 3A:
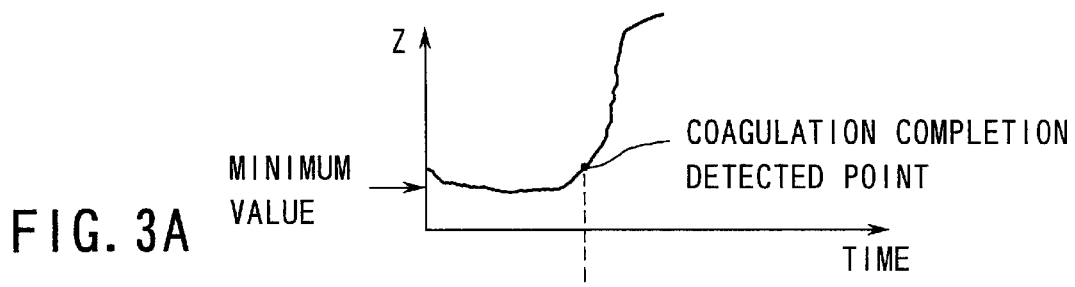
FIG. 3A is a graph showing an output of impedance according to the first embodiment and FIG. 3B is a graph showing change in the output and limiter value.
Figure 3B:
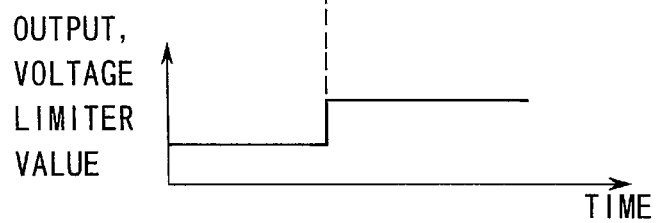

FIG. 3A is a graph showing the output characteristic of the impedance and FIG. 3B is a graph showing change in the characteristic of each of the output and the voltage limiter level.

Referring to FIGS. 3A and 3B, a moment of time indicated with a dashed line indicates a moment of time at which a coagulation point has been detected. Note that the foregoing graphs are applied to second to seventh embodiments to be described later.

As described above, according to the first embodiment, completion of coagulation can be detected to automatically employ an output load characteristic suitable to the incising operation. As a result, an undesirable incising operation is not performed in a state where coagulation is in an insufficient state. Thus, a safety operation can be performed. Since the rate of change in the impedance is monitored, an influence from an absolute value can be eliminated.

A second embodiment of the present invention will now be described.

Since the structure of an electric medical apparatus according to the second embodiment is the same as that according to the first embodiment, only the operation of the second embodiment will now be described.

Figure 5:
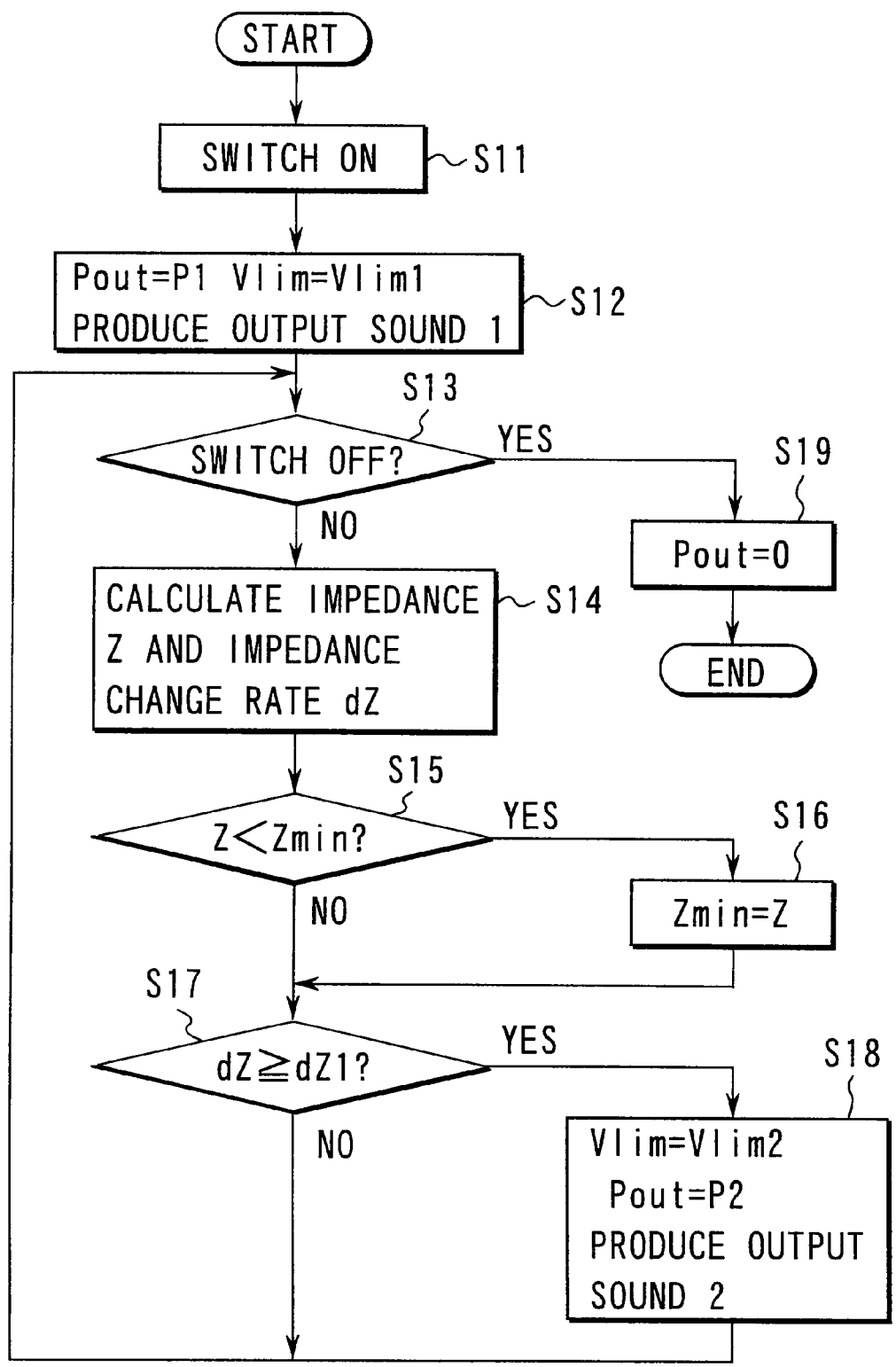
FIG. 5 is a flow chart showing the operation of an electric medical apparatus according to a second embodiment of the present invention.

FIG. 5 is a flow chart of the operation of the electric medical apparatus according to the second embodiment.

Figure 4:
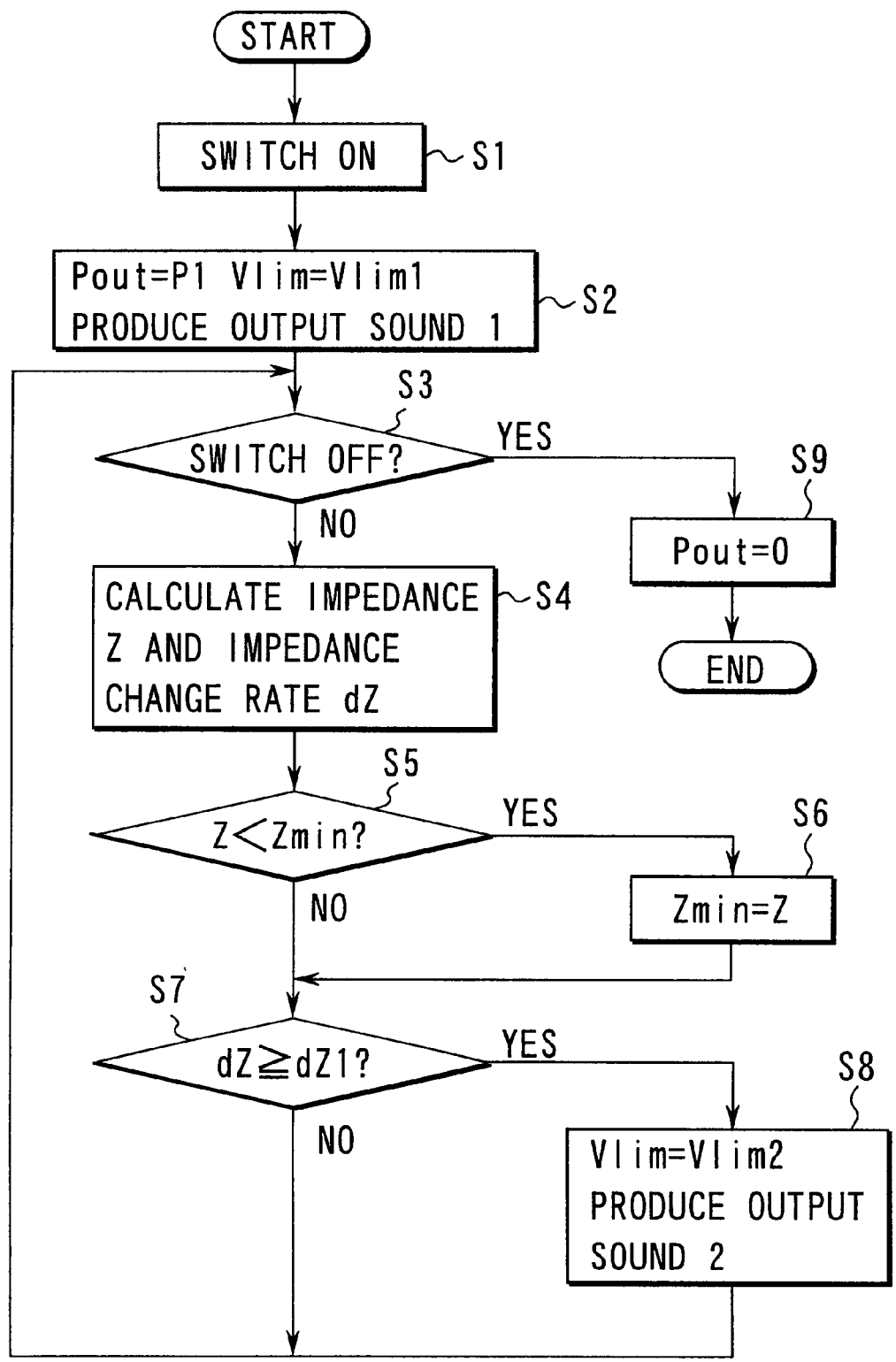
FIG. 4 is a flow chart showing the operation of the electric medical apparatus according to the first embodiment.

In the flow chart shown in FIG. 5, steps S11 to S17 and S19 are similar to steps S1 to S7 and S9 in the flow chart shown in FIG. 4 and according to the first embodiment. Therefore, similar operations are omitted from description.

When the impedance change rate dZ is, in step S17, larger than a predetermined value dZ1, the operation proceeds to step S18. In step S18 the voltage limiter level Vlim is set such that Vlim2=200V and the output electric power Pout is set such that P2=80 W. Moreover, output sound 2 is produced. As a result, the incising operation is started.

If the relationship dZ≧dZ1 is not satisfied in step S17 or if step S18 has been completed, the operation is returned to step S13.

According to the second embodiment, an effect similar to that obtainable from the first embodiment can be obtained.

A third embodiment of the present invention will now be described.

Since also the structure of an electric medical apparatus according to the third embodiment is the same as that according to the first embodiment, only the operation of the third embodiment will now be described.

Figure 6:
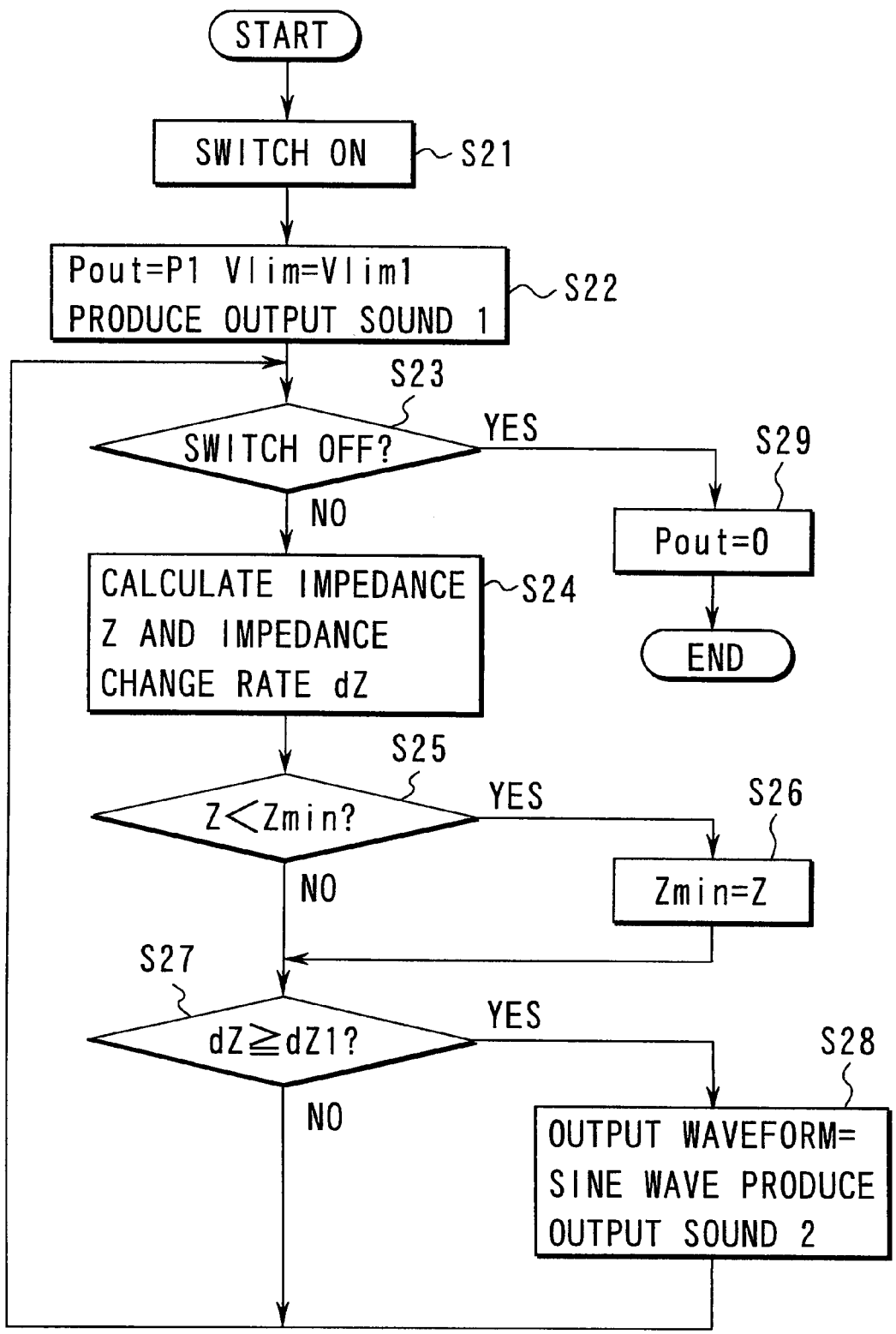
FIG. 6 is a flow chart showing the operation of an electric medical apparatus according to a third embodiment of the present invention.

FIG. 6 is a flow chart of the operation of the electric medical apparatus according to the third embodiment.

In the flow chart shown in FIG. 6, steps S21 to S27 and S29 are similar to steps S1 to S7 and S9 in the flow chart shown in FIG. 4 and according to the first embodiment. Therefore, similar operations are omitted from description.

If the impedance change rate dZ is, in step S27, larger than a predetermined value dZ1, the operation proceeds to step S28. In step S28 a burst wave which is the waveform of the initial output is changed to a sine wave. Moreover, output sound 2 is produced. The sine waveform of the output is suitable to the incising operation. Thus, the incising operation is started.

If the relationship dZ≧dZ1 is not satisfied in step S27 or if the process in step S28 has been completed, the operation is returned to step S23.

According to the third embodiment, an effect similar to that obtainable from the first embodiment can be obtained.

A fourth embodiment of the present invention will now be described.

Since also the structure of an electric medical apparatus according to the fourth embodiment is the same as that according to the first embodiment, only the operation of the fourth embodiment will now be described.

Figure 7:
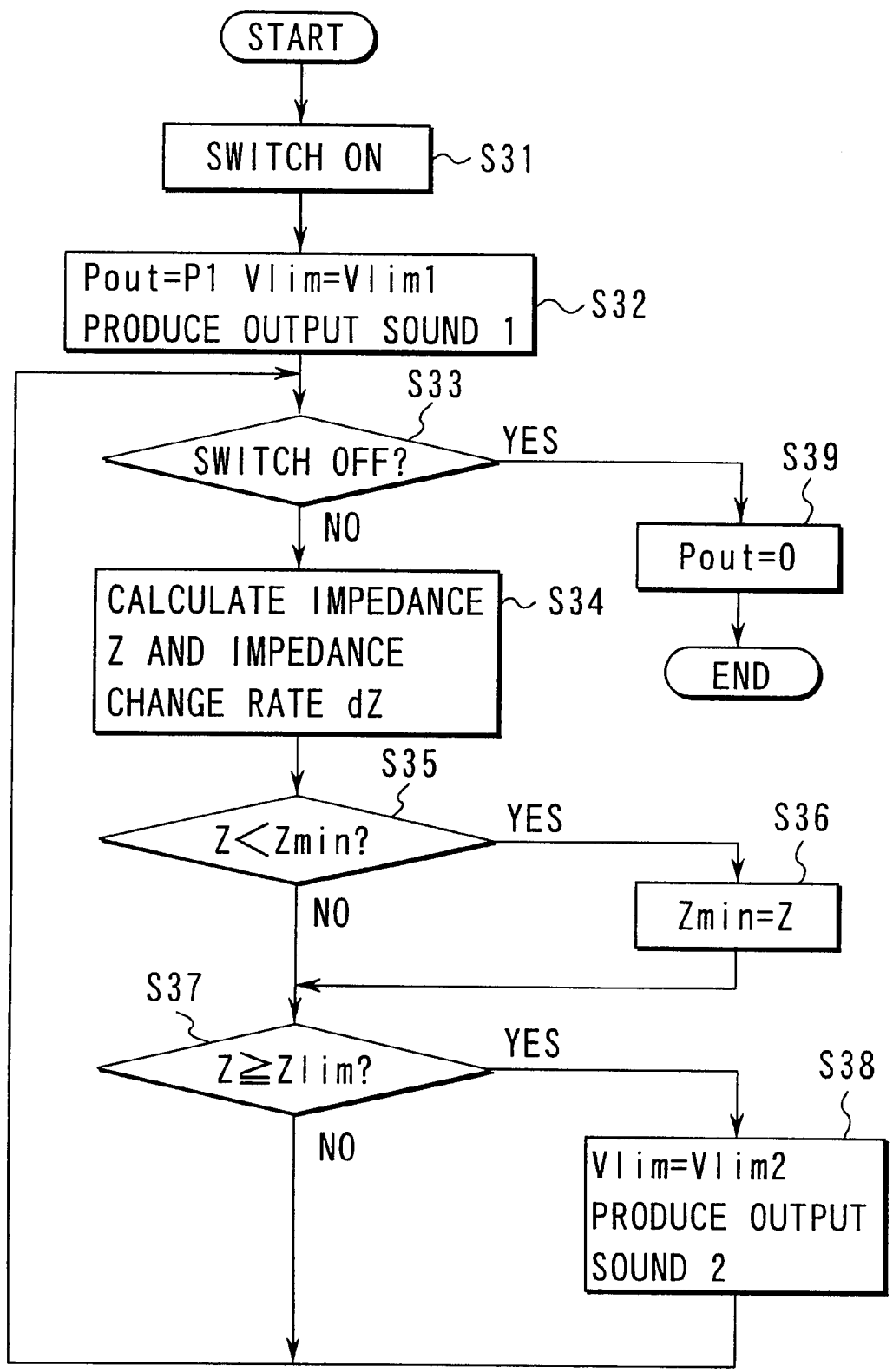
FIG. 7 is a flow chart showing the operation of an electric medical apparatus according to a fourth embodiment of the present invention.

FIG. 7 is a flow chart of the operation of the electric medical apparatus according to the fourth embodiment.

In the flow chart shown in FIG. 7, steps S31 to S36 and S39 are similar to steps S1 to S6 and S9 in the flow chart shown in FIG. 4 and according to the first embodiment. Therefore, similar operations are omitted from description.

If impedance Z is not smaller than an upper limit of Zlim, that is, Zlim=500Ω or greater in step S37 after step S35 or S36 has been completed, the operation proceeds to step S38. Thus, the voltage limiter level Vlim is set such that Vlim2=200V. Thus, output sound 2 is produced. Therefore, the incising operation is started.

If the relationship Z≧Zlim is not satisfied in step S37, the operation is returned from step S38 to step S33.

As described above, according to the fourth embodiment, completion of coagulation can be detected to automatically change the output load characteristic to that suitable to the incising operation. As a result, an undesirable incising operation is not performed in a state where coagulation is in an insufficient state. Thus, a safety operation can be performed. Since the absolute value of the impedance is monitored, a great effectiveness can be realized when a point, at which the impedance is apparently rapidly changed, cannot be detected.

The fourth embodiment has the structure that when the impedance Z is not smaller than the upper limit Zlim in step S37, the voltage limiter level Vlim is set such that Vlim2=200V and output sound 2 is produced. The present invention is not limited to this. For example, the settings in step S18 included in the flow chart shown in FIG. 5 may be employed in which the voltage limiter level Vlim is made such that Vlim2=200V, the output voltage Pout is made such that P2=80 W and production of output sound 2 is performed. Also the settings in step S28 included in the flow chart shown in FIG. 6 may be employed in which the sine wave output is employed and production of output sound 2 is performed.

A fifth embodiment of the present invention will now be described.

Since the structure of an electric medical apparatus according to the fifth embodiment is the same as that according to the first embodiment, only the operation of the fifth embodiment will now be described.

Figure 8:
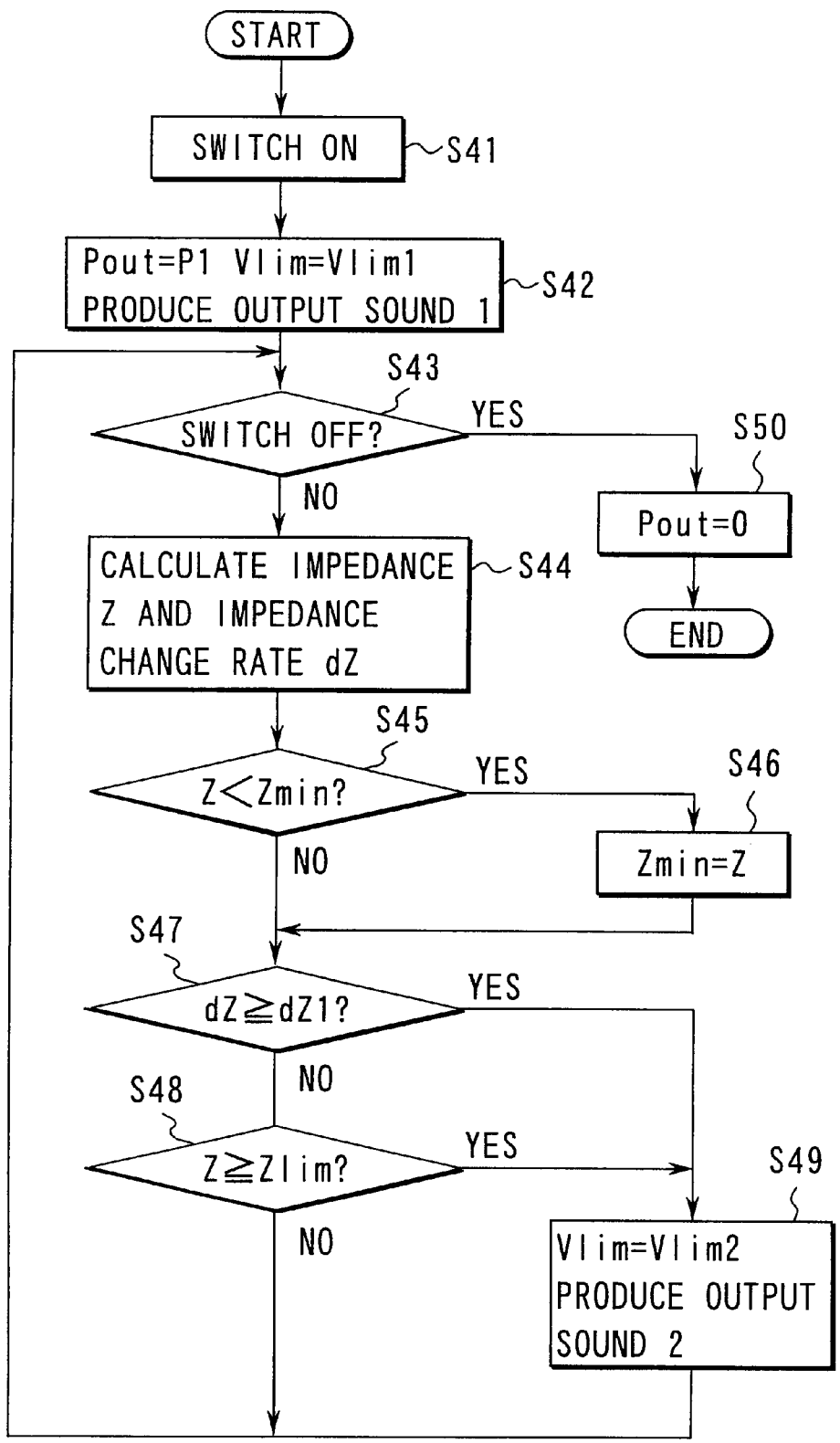
FIG. 8 is a flow chart showing the operation of an electric medical apparatus according to a fifth embodiment of the present invention.

FIG. 8 is a flow chart of the operation of the electric medical apparatus according to the fifth embodiment.

In the flow chart shown in FIG. 8, steps S41 to S46 and S50 are similar to steps S1 to S6 and S9 in the flow chart shown in FIG. 4 and according to the first embodiment. Therefore, similar operations are omitted from description.

If impedance change rate dZ is not smaller than the predetermined value dZ1 in step S47 or the impedance Z is not smaller than the upper limit Zlim in step S48 after step S45 or step S46, the operation proceeds to step S49. In step S49 the voltage limiter level Vlim is set such that Vlim2= 200V and output sound 2 is produced. As a result, the incising operation is started.

If the relationship Z≧Zlim is not satisfied in step S48 or if the process in step S49 has been completed, the operation is returned to step S43.

According to the fifth embodiment, completion of coagulation can be detected to automatically change the output load characteristic to that suitable to the incising operation. As a result, an undesirable incising operation is not performed in a state where coagulation is in an insufficient state. Thus, a safety operation can be performed. Since the two conditions are monitored, leakage in detection can satisfactorily be prevented.

Similarly to the fourth embodiment, the operation in step S49 may be replaced by step S18 included in the flow chart shown in FIG. 5 or step S28 included in the flow chart shown in FIG. 6.

A sixth embodiment of the present invention will now be described.

Since the structure of an electric medical apparatus according to the sixth embodiment is the same as that according to the first embodiment, only the operation of the sixth embodiment will now be described.

Figure 9:
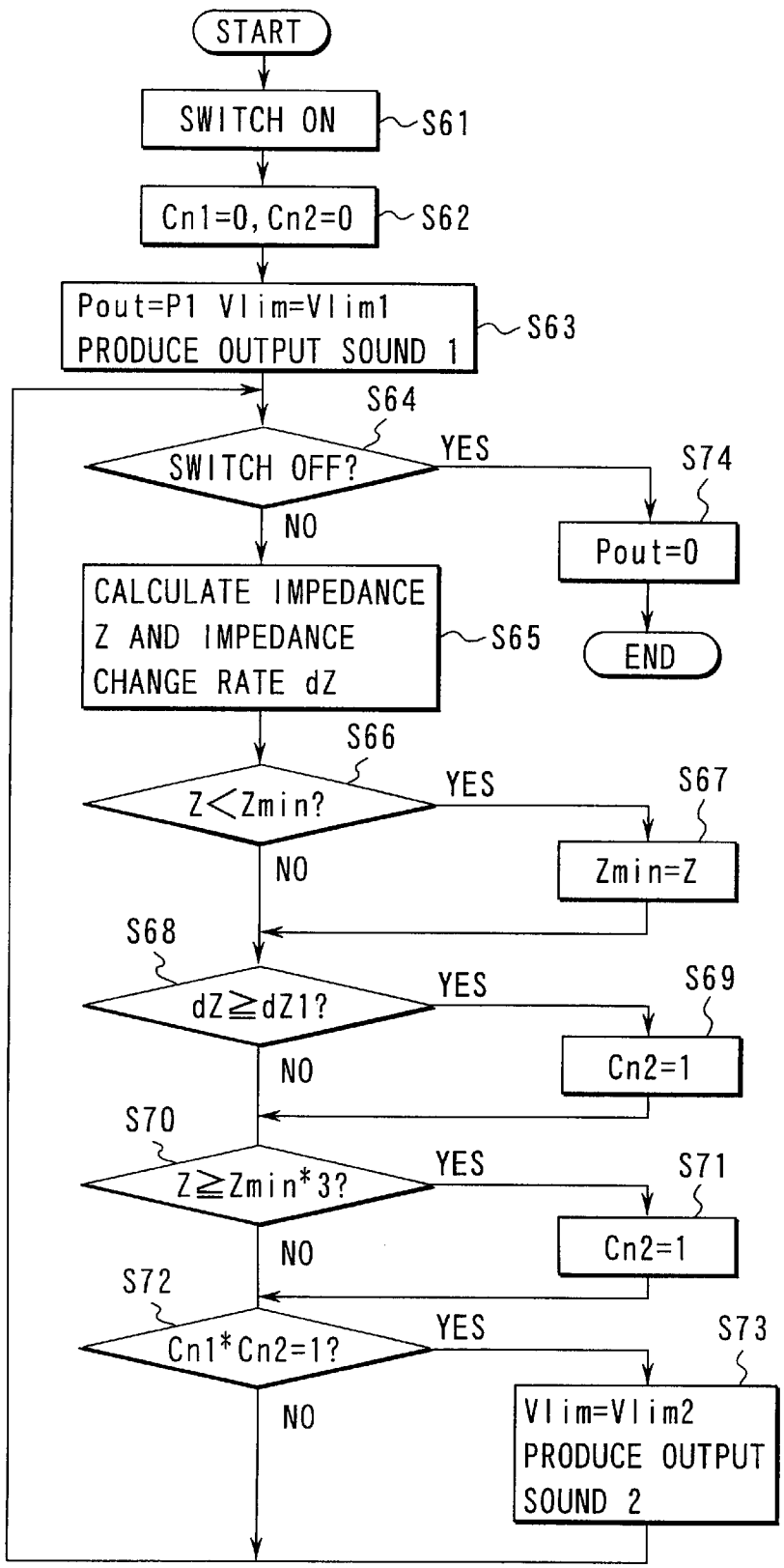
FIG. 9 is a flow chart showing the operation of an electric medical apparatus according to a sixth embodiment of the present invention.

FIG. 9 is a flow chart of the operation of the electric medical apparatus according to the sixths embodiment.

In the flow chart shown in FIG. 9, steps S61 and S63 to S67 and S74 are similar to steps S1, S2 to S6 and S9 in the flow chart shown in FIG. 4 and according to the first embodiment. Therefore, similar operations are omitted from description.

In step S61, the output switch is switched on, and then predetermined determination conditions Cn1 and Cn2 are initialized in step S62.

If the impedance change rate dZ is not smaller than the predetermined value dZ1 in step S68 after the operation in step S66 or step S67 has been completed, the operation proceeds to step S69. If a negative determination is made, the operation proceeds to step S70. In step S69, "1" is set to the determination condition Cn1.

In step S70 whether or not the impedance Z is not smaller than three times minimum value Zmin is determined. If impedance Z is not smaller than three times Zmin, the operation proceeds to step S71 so that "1" is set to the determination condition Cn2.

In step S72 whether or not impedance change rate dZ is not smaller than the predetermined value dZ1 and the impedance Z is three times or greater the minimum value Zmin is determined. If the conditions in step S72 are not satisfied, the operation proceeds to step S73 so that the voltage limiter level Vlim is set such that Vlim2=200V and output sound 2 is produced. As a result, the incising operation is started.

If the conditions in step S72 are not satisfied or if the operation in step S73 has been completed, the operation is returned to step S64.

According to the sixth embodiment, completion of coagulation can be detected to automatically change the output load characteristic to that suitable to the incising operation. As a result, an undesirable incising operation is not performed in a state where coagulation is in an insufficient state. Thus, a safety operation can be performed. Since the two conditions are combined with each other, completion of coagulation can reliably be detected.

Similarly to the fourth and fifth embodiments, the operation in step S73 may be replaced by step S18 included in the flow chart shown in FIG. 5 and step S28 included in the flow chart shown in FIG. 6.

A seventh embodiment of the present invention will now be described.

Since the structure of an electric medical apparatus according to the seventh embodiment is the same as that according to the first embodiment, only the operation of the seventh embodiment will now be described.

Figure 10:
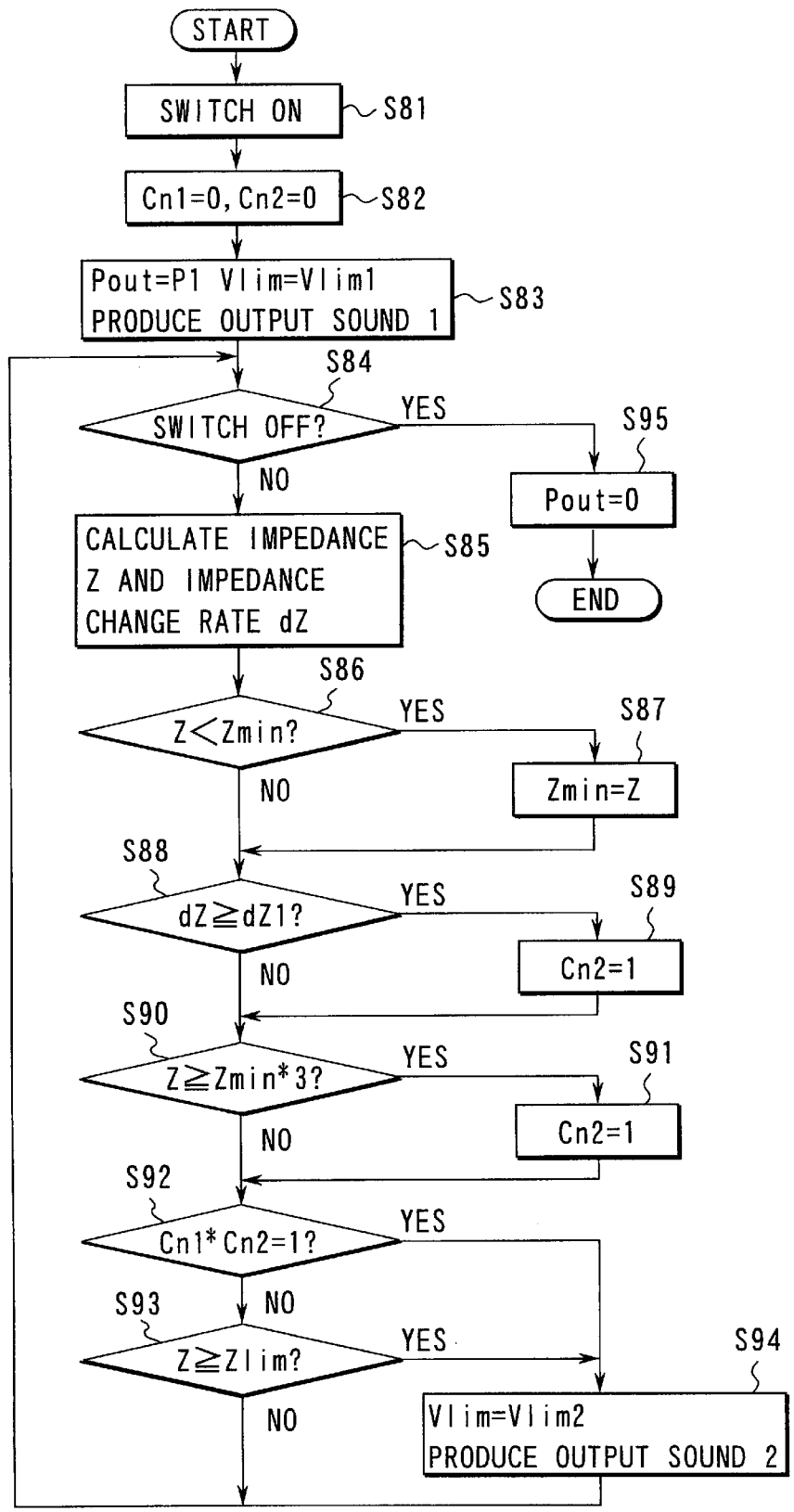
FIG. 10 is a flow chart showing the operation of an electric medical apparatus according to a seventh embodiment of the present invention.

FIG. 10 is a flow chart of the operation of the electric medical apparatus according to the seventh embodiment.

Step S81, S83 to S87 and S95 included in the flow chart shown in FIG. 10 are similar to step S1, S2 to S6 and S9 included in the flow chart shown in FIG. 4 and according to the first embodiment. Therefore, similar operations are omitted.

In step S81, the output switch is switched on, and then the predetermined determination conditions Cn1 and Cn2 are initialized in step S82.

In steps S88 to S91 conditions are set similarly to steps S68 to S71 shown in FIG. 9. That is, if the impedance change rate dZ is not smaller than the predetermined value dZ1 in step S88, the operation proceeds to step S89 so that "1" is set to the determination condition Cn1.

In step S90 whether or not the impedance Z is three times or greater the minimum value Zmin is determined. If impedance Z is three times or greater Zmin, the operation proceeds to step S91 so that "1" is set to the determination condition Cn2.

In steps S92 and S93 the following conditions are determined. If the impedance change rate dZ is not smaller than the predetermined value dZ1 and the impedance Z is not smaller than three times the minimum value Zmin in step S92, or if the impedance Z is not smaller than the upper limit Zlim in step S93, the operation proceeds to step S94. In step S94 the voltage limiter level Vlim is set such that Vlim2= 200V and output sound 2 is produced. As a result, the incising operation is started.

If any one of the conditions in steps S92 and S93 is not satisfied, or if the operation in step S94 has been completed, the operation is returned to step S84.

According to the seventh embodiment, completion of coagulation can be detected to automatically change the output load characteristic to that suitable to the incising operation. As a result, an undesirable incising operation is not performed in a state where coagulation is in an insufficient state. Thus, a safety operation can be performed. Since the plural conditions are combined with one another, completion of coagulation can reliably be detected and leakage in detection can satisfactorily be prevented.

Similarly to the fourth to sixth embodiments, the operation in step S94 may be replaced by step S18 included in the flow chart shown in FIG. 5 or step S28 included in the flow chart shown in FIG. 6.

Figures 11A, 11B:
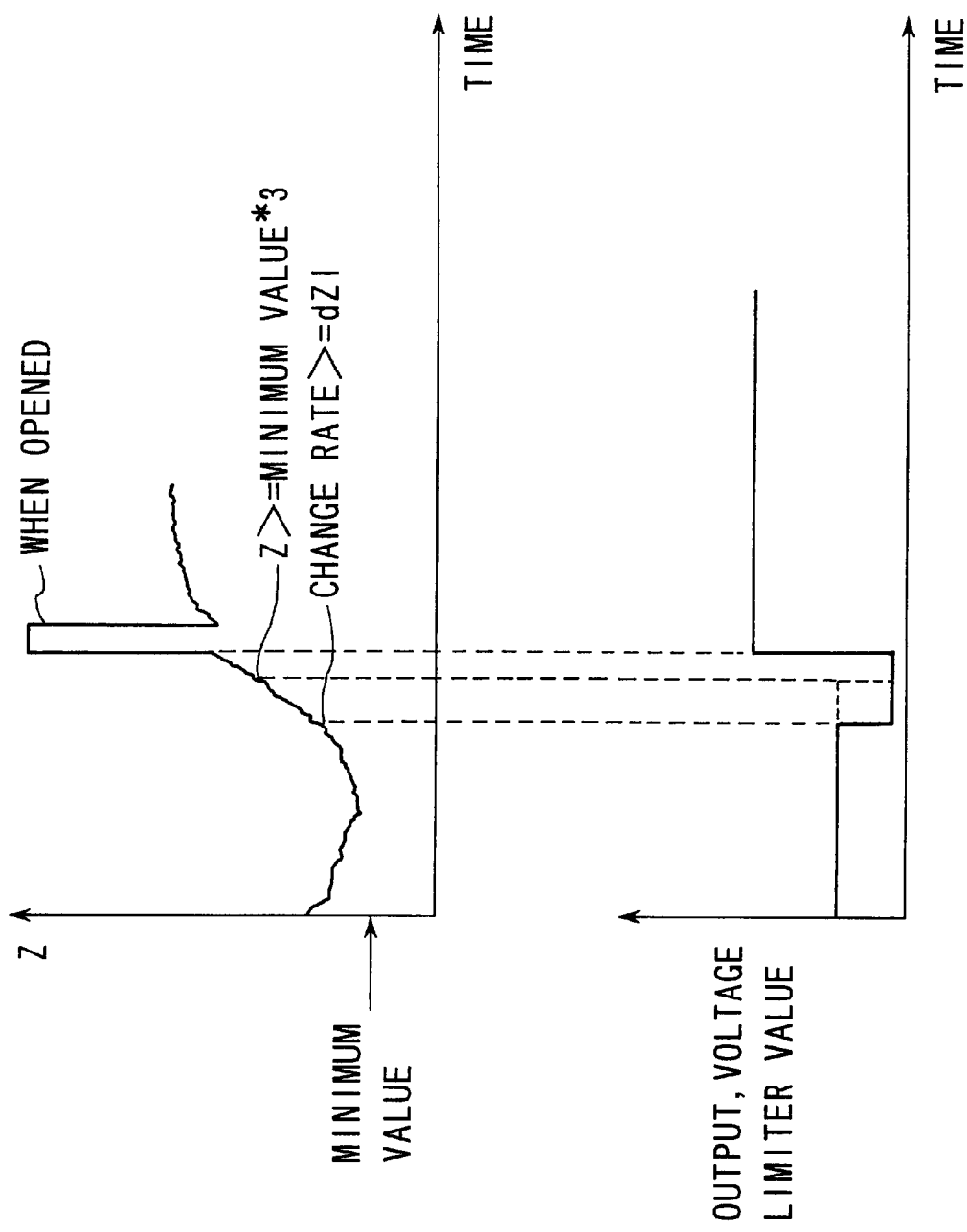
FIG. 11A is a graph showing the output of impedance according to an eighth embodiment of the present invention and FIG. 11B is a graph showing change in the output and voltage limiter levels according to the eighth embodiment.
Figure 12:
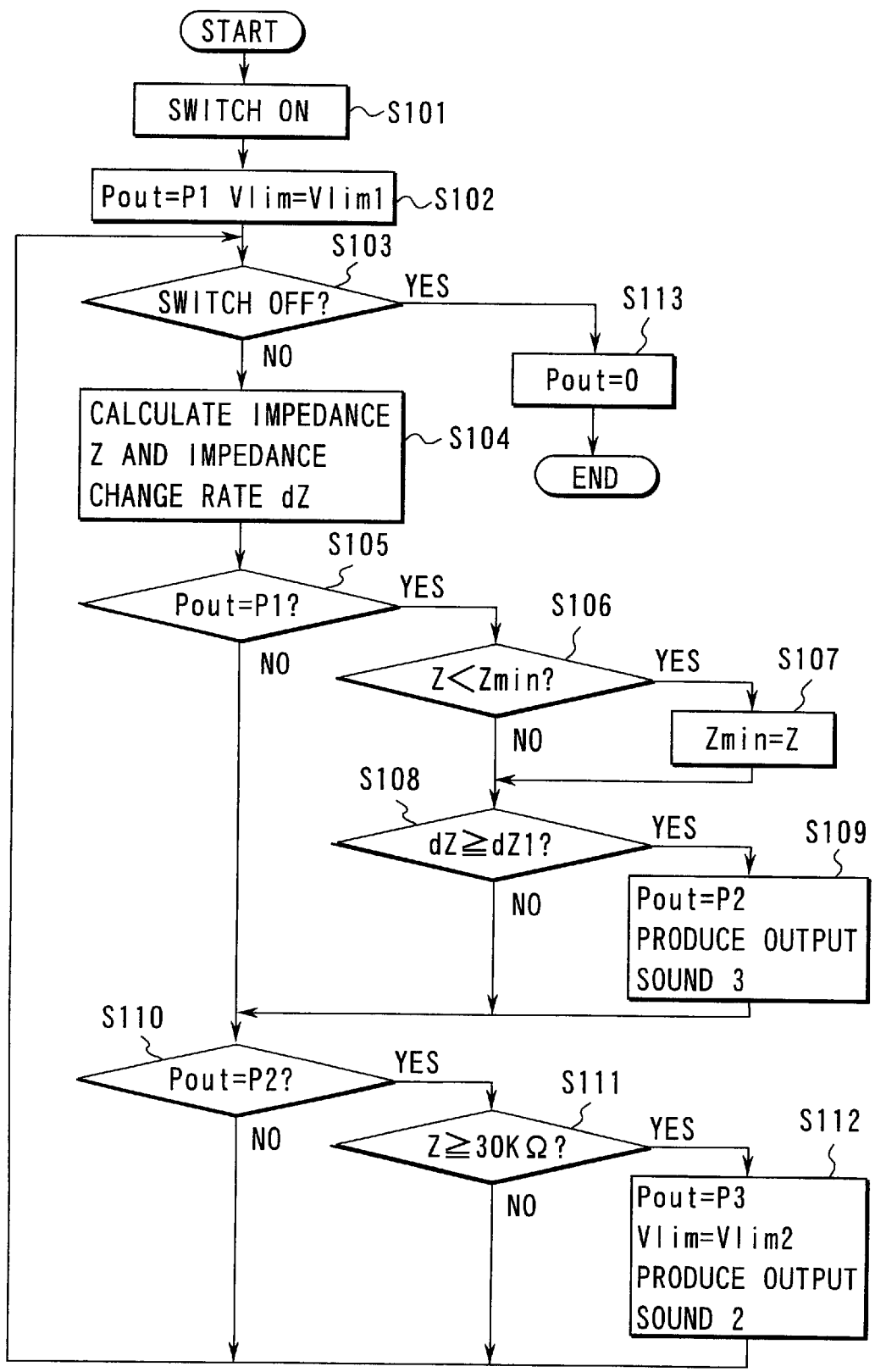
FIG. 12 is a flow chart showing the operation of an electric medical apparatus according to the eighth embodiment of the present invention.

Referring to FIGS. 11A, 11B and 12, an eighth embodiment of the present invention will now be described.

Since the structure of an electric medical apparatus according to the eighth embodiment is the same as that according to the first embodiment, only the operation of the eighth embodiment will now be described.

The first to seventh embodiments have the structure that the automatic incising process is started immediately after completion of coagulation. In the eighth embodiment, a confirmation period of time is permitted for an operator after coagulation has been completed as shown in the graphs shown in FIGS. 11A and 11B.

Referring to a flow chart shown in FIG. 12, the operation of the electric medical apparatus according to the eighth embodiment of the present invention will now be described.

When a normal mode-selection is performed, either of output switches (not shown) corresponding to coagulation and incision is depressed to perform a required output. When an automatic coagulation/incision mode selection is performed, the following operation is performed when the incision switch has been depressed.

When the foot switch 14 or a hand switch (not shown) is switched on in step S101, output is started such that output electric power (Pout) satisfies P1=40 W and a voltage limiter level (Vlim) satisfies Vlim=60V. At this time, output sound 1 is produced. The foregoing output has an output load characteristic suitable to coagulating the organism.

In step S103 the state of the output switch is determined. When the switch has been switched on, the operation proceeds to step S104. Thus, measured values are acquired from the voltage sensor 38 and the current sensor 40 so that impedance Z and impedance change rate dZ are calculated.

In step S105 whether or not the output Pout satisfies P1=40 W is determined. If the relationship Pout=P1 is not satisfied, the operation proceeds to step S110. If the relationship Pout=P1 is satisfied, the operation proceeds to step S106.

In step S106 the calculated value of the impedance Z is compared with the minimum value Zmin. If the impedance is the minimum value, the operation proceeds to step S107 so that the minimum impedance value is stored as Zmin. If the impedance Z is not smaller than the minimum value Zmin, the operation proceeds to step S108.

In step S108 whether or not the impedance change rate dZ is not smaller than dZ1=+300 Ω/sec which is a predetermined value is determined. If dZ≧dZ1, the operation proceeds to step S109 so that the output Pout is set such that P2=10 W and output sound 3 is produced.

In step S110 whether or not the output Pout satisfies P2=10 W is determined. The operation is returned to step S103 until the foregoing condition is satisfied. That is, measurement of the impedance is repeated. If Pout=P2 in step S110, the operation proceeds to step S111 so that whether or not the impedance Z is not smaller than 30 kΩ is determined.

If the impedance Z is 30 kΩ or greater, a determination is made that the operator has loosened the hand holding the bipolar cutting forceps 12. That is, a determination is made that switching has been confirmed. Thus, the operation proceeds to step S112. The reason for this lies in that confirmation of switching from the completed coagulation operation to the incising operation by the operation of the operator to loosen the forceps enables the operation to reliably be performed.

In step S112 the output Pout is set such that P3=80 W and the voltage limiter level Vlim is set such that Vlim2=200V. Moreover, output sound 2 is produced. Thus, an output load characteristic suitable to the incising operation is realized. Thus, the incising operation is started.

If the conditions in steps S110 and S111 are not satisfied, the operation is returned to step S103 after step S112 has been completed.

If a determination is made at an arbitrary moment of time in step S103 that the switch has been switched off, the operation proceeds to step S113 so that the output is interrupted.

As described above, according to the eighth embodiment, proceeding of coagulation is detected to reduce the output so as to prevent excessive burning can be prevented. Moreover, the output can automatically be changed to be suitable to the incising operation when the incising operation has been started.

A ninth embodiment of the present invention will now be described.

Since the structure of an electric medical apparatus according to the ninth embodiment is the same as that according to the first embodiment, only the operation of the ninth embodiment will now be described.

Figure 13:
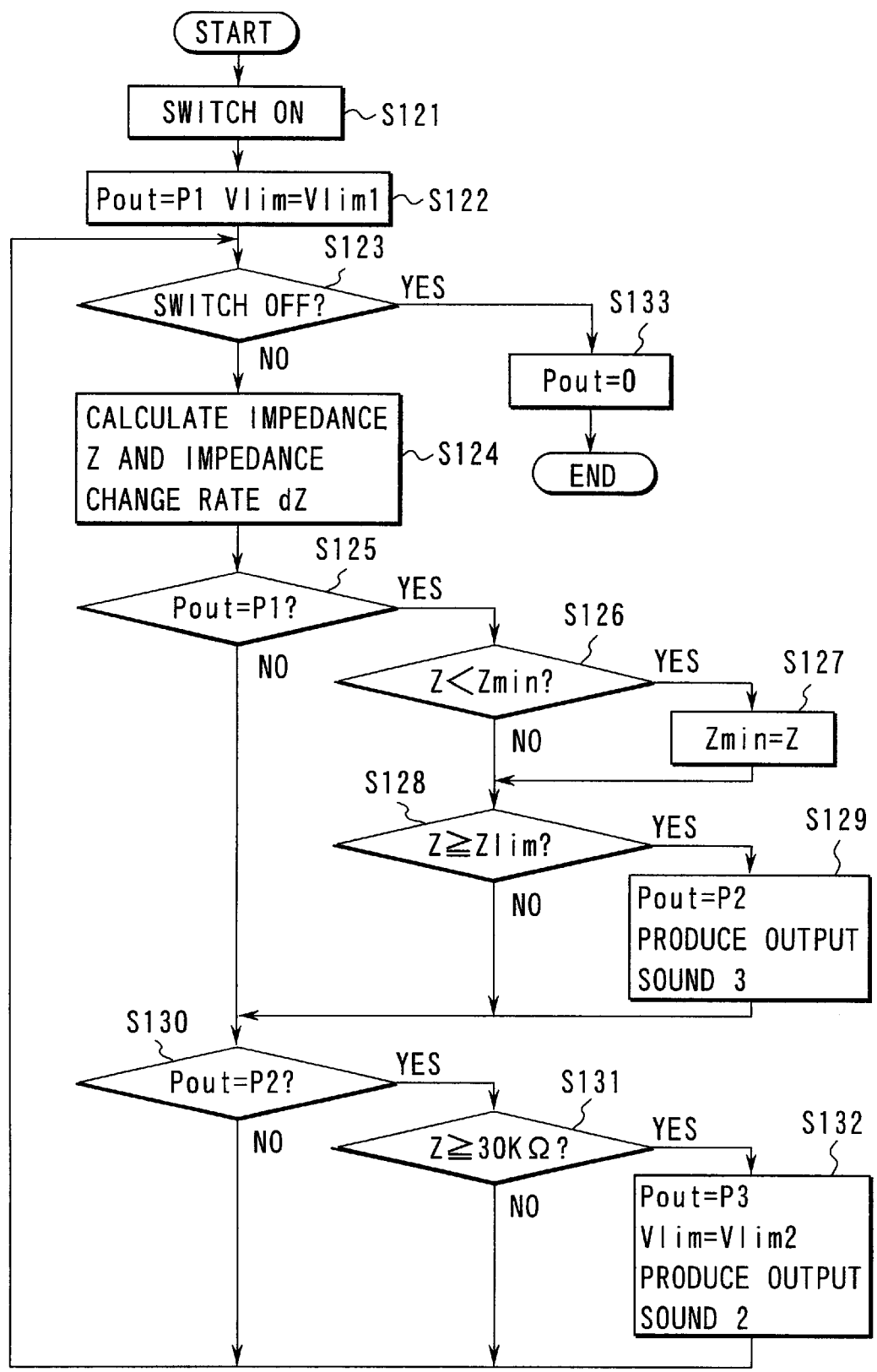
FIG. 13 is a flow chart showing the operation of an electric medical apparatus according to a ninth embodiment of the present invention.

FIG. 13 is a flow chart of the operation of the electric medical apparatus according to the ninth embodiment.

In the flow chart shown in FIG. 13, steps S121 to S127 and steps S129 to S133 are similar to steps S101 to S107 and steps S109 to S113 in the flow chart shown in FIG. 12 according to the eighth embodiment. Therefore, similar operations are omitted from description.

If impedance Z is not smaller than minimum value Zmin in step S126 or if step S127 has been completed, the operation proceeds to step S128. In step S128 whether or not the impedance Z is not smaller than the upper limit Zlim is determined. If the impedance Z is not smaller than the upper limit Zlim, the operation proceeds to step S129. If a negative determination is made, the operation proceeds to step S130.

According to the ninth embodiment, an effect similar to that obtainable from the eighth embodiment can be obtained.

A tenth embodiment of the present invention will now be described.

Since the structure of an electric medical apparatus according to the tenth embodiment is the same as that according to the first embodiment, only the operation of the tenth embodiment will now be described.

Figure 14:
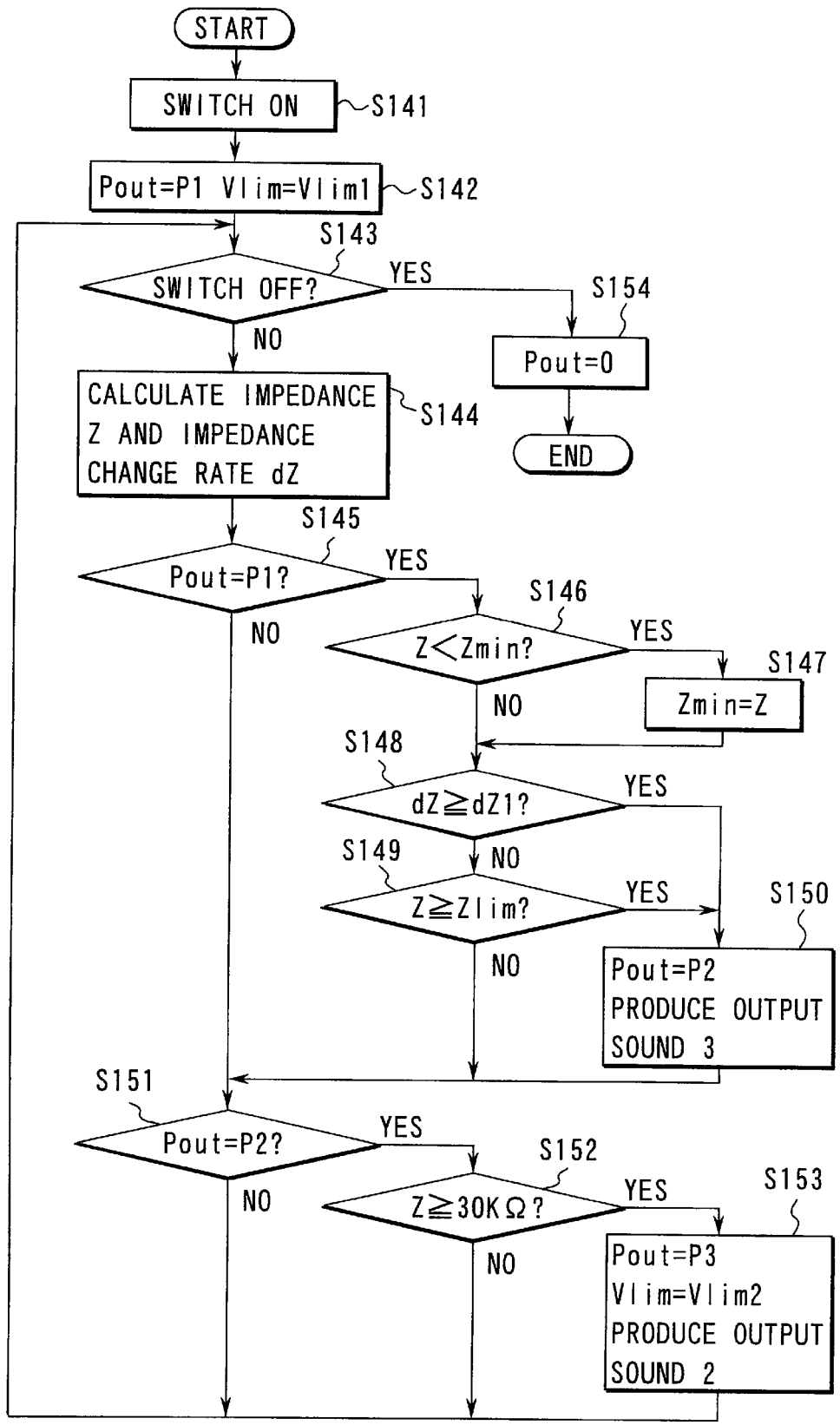
FIG. 14 is a flow chart showing the operation of an electric medical apparatus according to a tenth embodiment of the present invention.

FIG. 14 is a flow chart of the operation of the electric medical apparatus according to the tenth embodiment.

In the flow chart shown in FIG. 14, steps S141 to S147 and steps S150 to S154 are similar to steps S101 to S107 and steps S109 to S113 in the flow chart shown in FIG. 12 and according to the eighth embodiment. Therefore, similar operations are omitted from description.

If impedance Z is not smaller than minimum value Zmin in step S146 or if step S147 has been completed, the operation proceeds to step S148. If the impedance change rate dZ is not higher than a predetermined level dZ1 in step S148, or if the impedance Z is not smaller than the upper limit Zlim in step S149, the operation proceeds to step S150.

If any condition in steps S148 and S149 is not satisfied, the operation proceeds to step S151 after step S150 has been completed.

According to the tenth embodiment, an effect similar to that obtainable from the eighth embodiment can be obtained.

An eleventh embodiment of the present invention will now be described.

Since the structure of an electric medical apparatus according to the eleventh embodiment is the same as that according to the first embodiment, only the operation of the eleventh embodiment will now be described.

Figure 15:
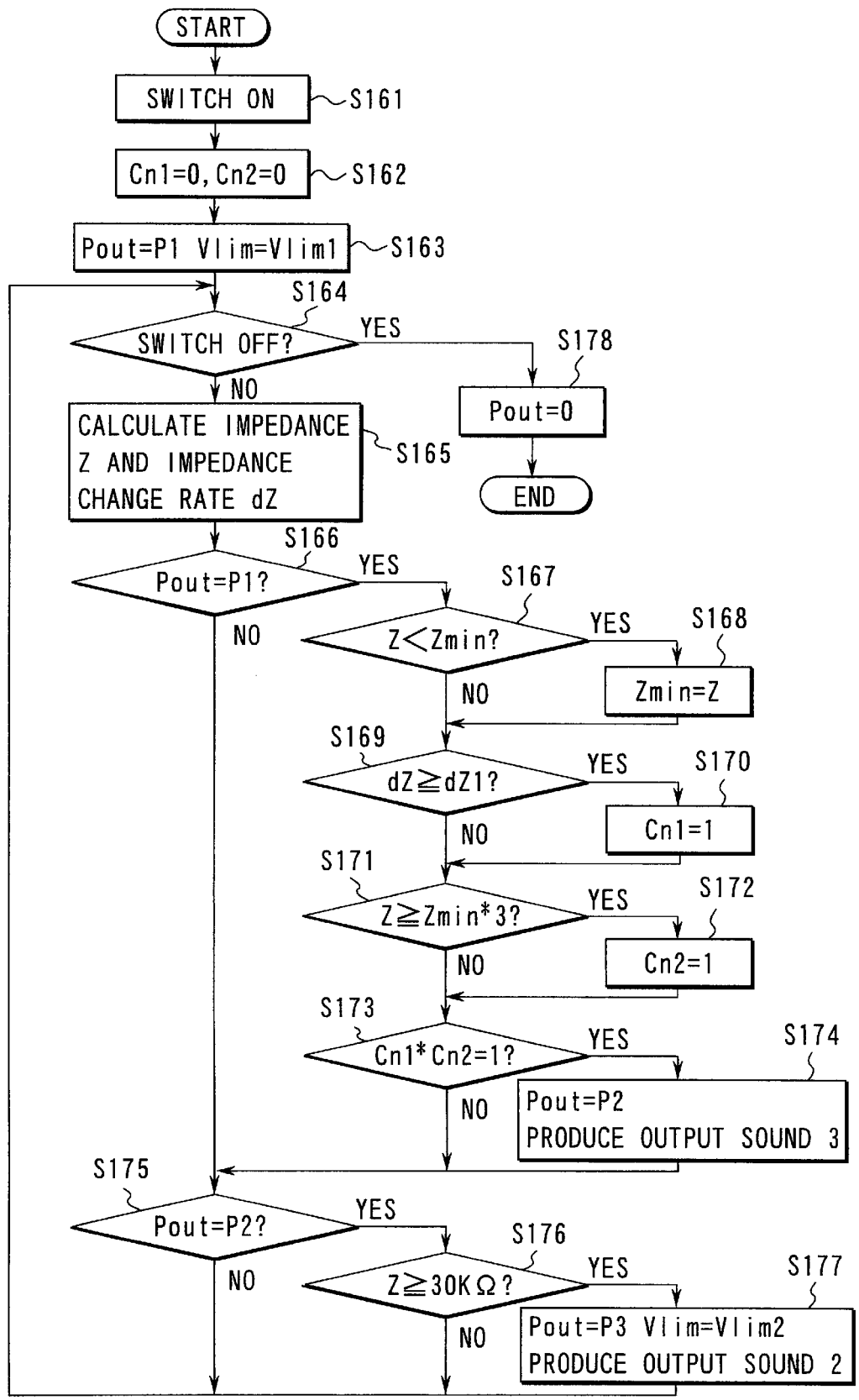
FIG. 15 is a flow chart showing the operation of an electric medical apparatus according to an eleventh embodiment of the present invention.

FIG. 15 is a flow chart of the operation of the electric medical apparatus according to the eleventh embodiment.

In the flow chart shown in FIG. 15, steps 161, S163 to 168 and steps S174 to S178 are similar to steps S101, S102 to S107 and steps S109 to S113 in the flow chart shown in FIG. 12 according to the eighth embodiment. Therefore, similar operations are omitted from description.

In step S161 the output switch is switched on, and then predetermined determination conditions Cn1 and Cn2 are initialized in step S162.

If the impedance Z is not smaller than the minimum value Zmin in step S167 or if step S168 has been completed, the operation proceeds to step S169. If the impedance change rate dZ is not smaller than the predetermined dZ1 in step S169, the operation proceeds to step S170. If a negative determination is made, the operation proceeds to step S171. In step S170, "1" is set to the determination condition Cn1.

In step S171 whether or not the impedance Z is three times or more the minimum value Zmin is determined. If impedance Z is three or more times Zmin, the operation proceeds to step S172 so that "1" is set to the determination condition Cn2.

In step S173 whether or not the impedance change rate dZ is not smaller than the predetermined value dZ1 and the impedance Z is three or more times the minimum value Zmin is determined. If the conditions in step S173 are satisfied, the operation proceeds to step S174.

According to the eleventh embodiment, an effect similar to that obtainable from the eighth embodiment can be obtained.

A twelfth embodiment of the present invention will now be described.

Since the structure of an electric medical apparatus according to the twelfth embodiment is the same as that according to the first embodiment, only the operation of the twelfth embodiment will now be described.

Figure 16:
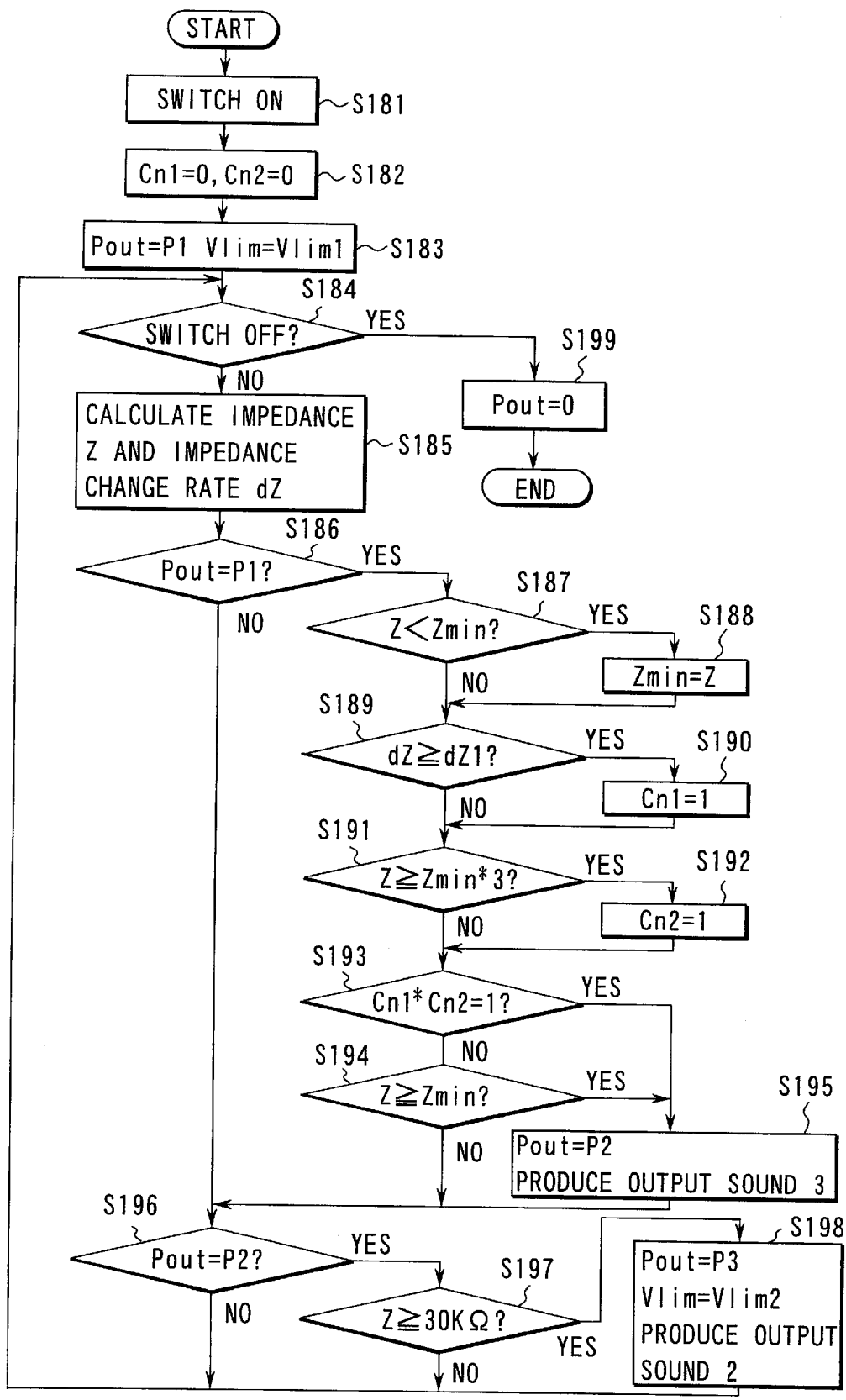
FIG. 16 is a flow chart showing the operation of an electric medical apparatus according to a twelfth embodiment of the present invention.

FIG. 16 is a flow chart of the operation of the electric medical apparatus according to the twelfth embodiment.

In the flow chart shown in FIG. 16, steps S181, S183 to S188 and steps S195 to S199 are similar to steps S101, S102 to S107 and steps S109 to S113 in the flow chart shown in FIG. 12 according to the eighth embodiment. Therefore, similar operations are omitted from description.

The output switch is switched on in step S181, and then the predetermined determination conditions Cn1 and Cn2 are initialized.

If impedance Z is not smaller than the minimum value Zmin in step S187, or if step S188 has been completed, the operation proceeds to step S189. If the impedance change rate dZ is not smaller than the predetermined value dZ1 in step S189, the operation proceeds to step S190 so that "1" is set to the determination condition Cn1.

In step S191 whether or not the impedance Z is three or more times the minimum value Zmin is determined. If impedance Z is three or more times Zmin, the operation proceeds to step S192 so that "1" is set to the determination condition Cn2.

In steps S193 and S194 the following conditions are satisfied. That is, if the impedance change rate dZ is not smaller than the predetermined value dZ1 and the impedance Z is three or more times the minimum value Zmin in step S193, or if the impedance Z is not smaller than the upper limit Zlim in step S194, the operation proceeds to step S195.

According to the twelfth embodiment, an effect similar to that obtainable from the eighth embodiment can be obtained.

A thirteenth embodiment of the present invention will now be described.

Figure 17:
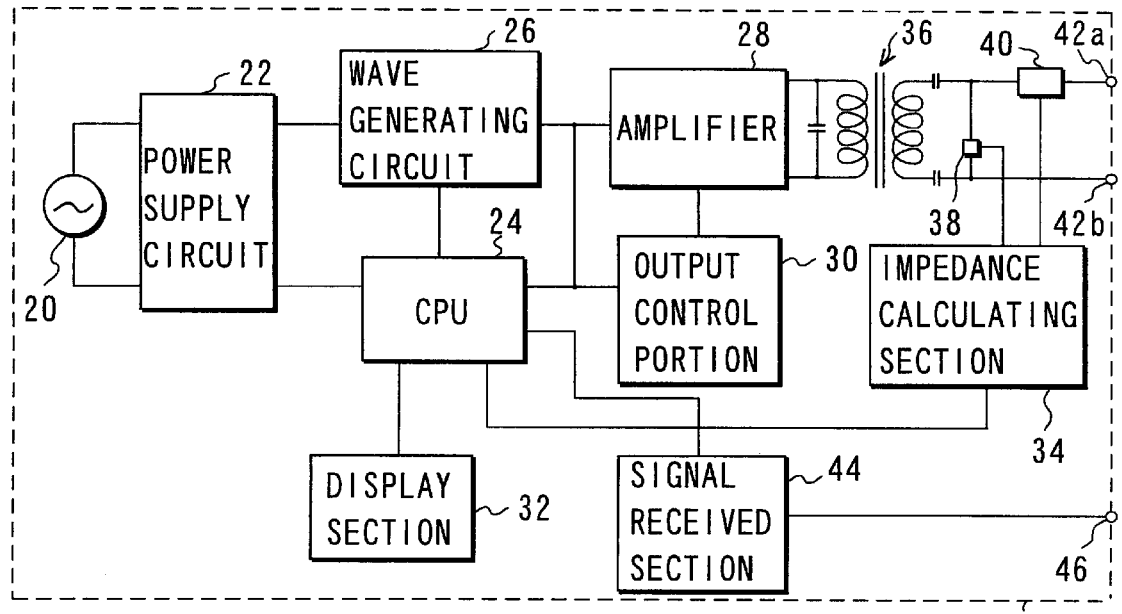
FIG. 17 is a diagram showing the electrical structure of an electric knife according to a thirteenth embodiment of the present invention.

FIG. 17 is a diagram showing the electrical structure of an electric knife body 10'. Note that elements shown in FIG. 17 which are the same as those shown in FIG. 1 are given the same reference numeral and omitted from description.

Referring to FIG. 17, a signal receiving portion 44 is connected to the CPU 24. Thus, a signal transmitted from a bipolar cutting forceps can be received through a terminal 46. As a result, the condition can be switched in response to the signal transmitted when the state in which the forceps is held has been changed.

Figure 18A:
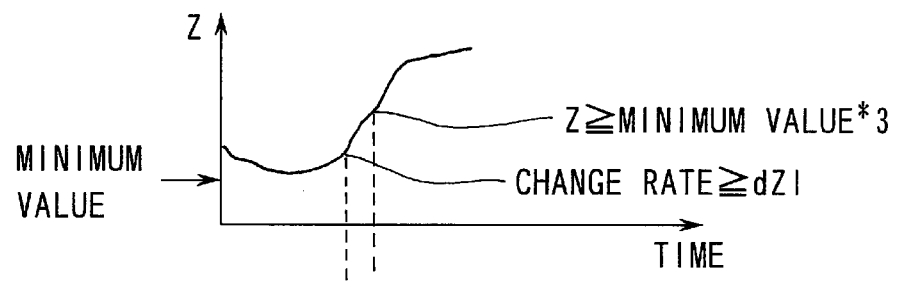
FIG. 18A is a graph showing impedance according to a thirteenth embodiment and FIG. 18B is a graph showing the output according to the thirteenth embodiment.
Figure 18B:
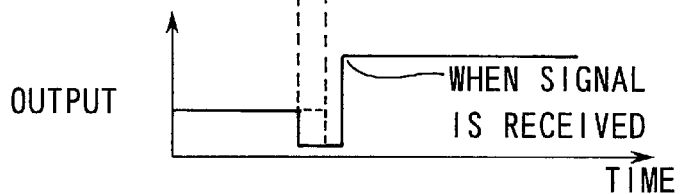

FIGS. 18A and 18B are graphs showing impedance and an output according to the thirteenth embodiment.

Figure 19:
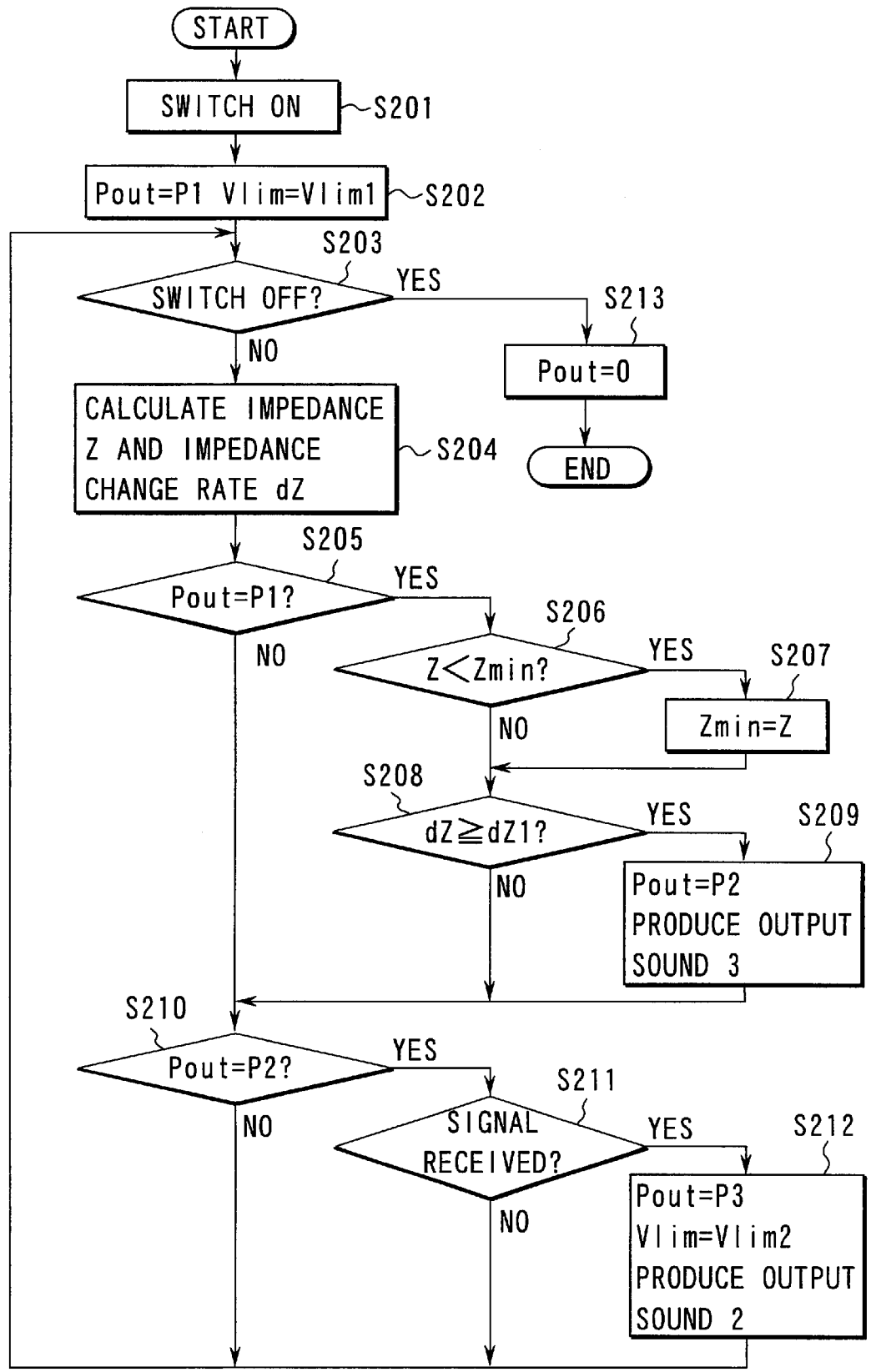
FIG. 19 is a flow chart showing the operation of an electric medical apparatus according to the thirteenth embodiment of the present invention.

FIG. 19 is a flow chart of the operation of the electric medical apparatus according to the thirteenth embodiment.

In the flow chart shown in FIG. 19, steps S201 to S210 and steps S212 and S213 are similar to steps S101 to S110 and steps S112 to S113 in the flow chart shown in FIG. 12 according to the eighth embodiment. Therefore, similar operations are omitted from description.

If Pout=P2 in step S210, the operation proceeds to step S211 so that whether or not a signal from outside has been received by the signal receiving portion 44 is determined. If the signal has been received, the operation proceeds to step S212. If the signal has not been received, the operation is returned to step S203.

That is, if a signal in synchronization with change in a state in which the forceps is held is received after the output has been reduced, the output and the voltage limiter level are raised. Moreover, output sound 3 is produced.

In the thirteenth embodiment, only the operation in a case where the signal has been received or only the voltage limiter level may be changed. As an alternative to this, the waveform of the output may be switched.

According to the thirteenth embodiment, an effect similar to that obtainable from the twelfth embodiment can be obtained.

Figure 20A:
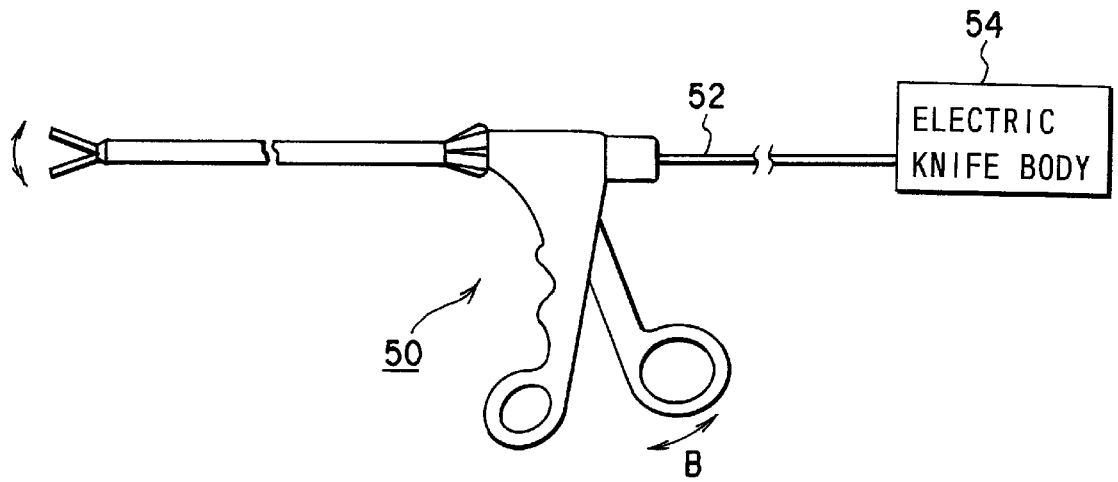
Figure 20B:
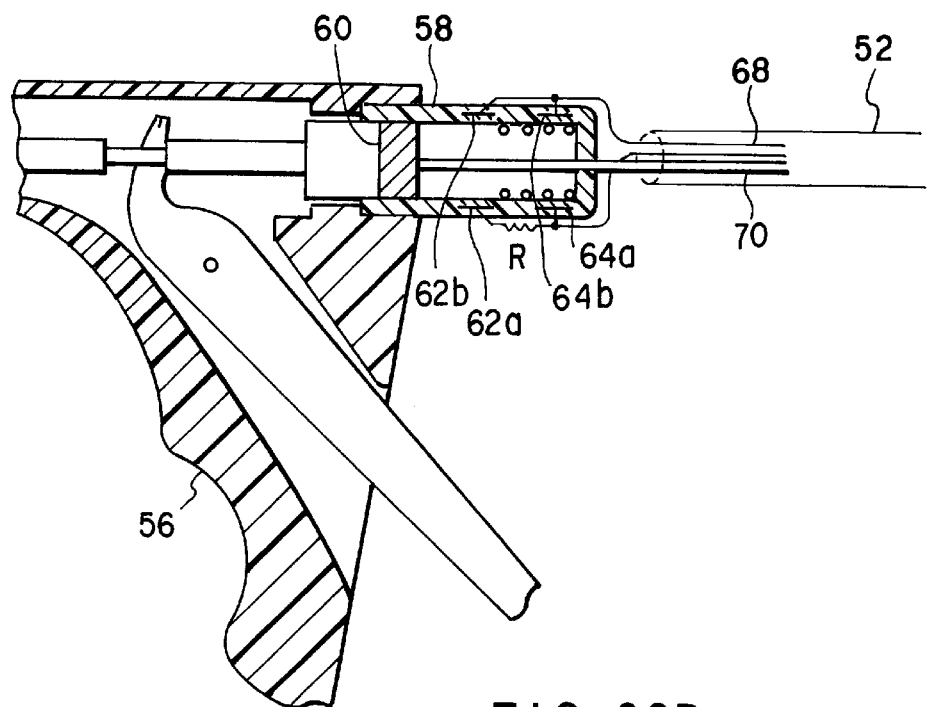
Figure 21:
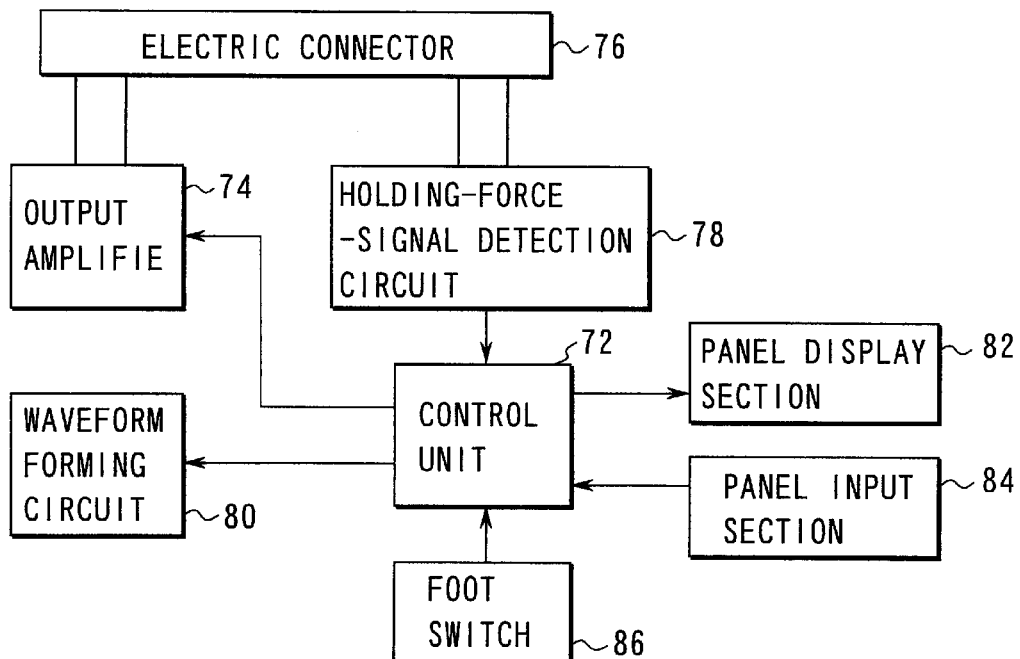
FIG. 21 is a block diagram showing the electrical structure of a portion including the electric knife body shown in FIG. 20A.
Figure 22:
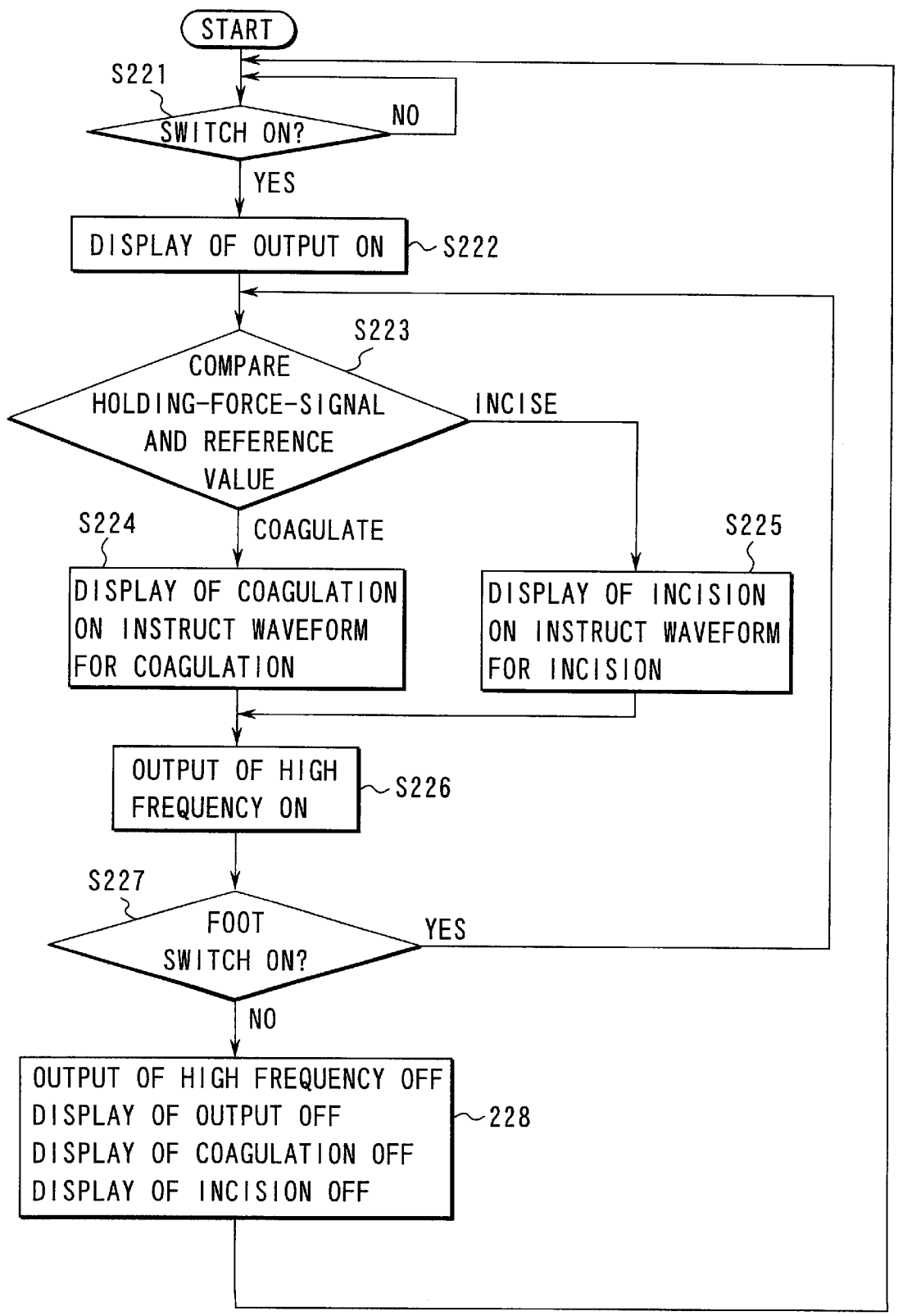
FIG. 22 is a flow chart showing the operation of an electric medical apparatus according to a fourteenth embodiment of the present invention.

Referring to FIGS. 20 to 22, a fourteenth embodiment of the present invention will now be described.

FIG. 20A is a diagram showing an example of the structure of an electric medical apparatus. FIG. 20B is an enlarged cross sectional view showing a portion of a holding portion of a bipolar cutting forceps shown in FIG. 20A.

Referring to FIG. 20A, a bipolar cutting forceps 50 is connected to an electric knife body 54 through a connection cable 52. A connection portion 58 is formed in the rear of a holding portion 56 which is a handle for the bipolar cutting forceps 50.

As shown in FIG. 20B, the connection portion 58 includes a movable electrode 60 which is slidable for a distance in accordance with an amount of holding of the handle which can be rotated in a direction indicated by an arrow B shown in FIG. 20A. Moreover, the connection portion 58 includes electrodes 62a, 62b, 64a and 64b disposed on the inner wall of the connection portion 58 and permitted to electrically be conducted to the movable electrode 60. The connection cable 52 includes a signal cable 68 for a holding-force signal, the signal cable 68 being connected to the electrodes 62a, 62b, 64a and 64b. Moreover, the connection cable 52 includes an output cable 70 connected to the movable electrode 60 and arranged to be used in a curing operation. Note that a resistance R is connected between the electrodes 62a and 64a to make the resistance value to be varied after conduction has been established.

FIG. 21 is a block diagram showing the electrical structure of a portion including the electric knife body shown in FIGS. 20A and 20B.

Referring to FIG. 21, an output amplifier 74, a holding-force-signal detection circuit 78 for receiving a signal representing an amount of gripping of the handle from the electric connector 76 connected to the bipolar cutting forceps 50 and a waveform forming circuit 80 are connected to a control unit 72 for totally controlling the apparatus. Moreover, a panel display portion 82, a panel input portion 84 and a foot switch 86, which is an output switch, are connected to the control unit 72.

Referring to a flow chart shown in FIG. 22, the operation of the fourteenth embodiment will now be described.

If a fact that the foot switch 86 has been switched on is confirmed in step S221, display of the output on the panel display portion 82 is started in step S222.

In step S223 the holding-force signal and a predetermined reference value are subjected to a comparison. The holding-force signal represents an analog value in proportion to an amount of gripping of the handle of the holding portion 56 of the bipolar cutting forceps 50 or a holding pressure applied to the leading end. As the handle is gripped, the movable electrode 60 in the connection portion 58 is moved. Thus, the movable electrode 60 is conducted to the electrodes 62a and 62b at a certain moment of time. As described above, the holding-force signal transmitted in a period in which the electrodes 62a and 62b are conducted is subjected to a comparison with the reference value. As a result, a determination is made that a coagulation output is being made, and then the operation proceeds to step S224.

If the handle is furthermore gripped in the state of the coagulation output, the movable electrode 60 is moved to open the electrodes 62a and 62b. Then, the movable electrode 60 is conducted to the electrodes 64a and 64b. As described above, the holding-force signal transmitted during conduction of the electrodes 64a and 64b is subjected to the comparison with the reference value. Thus, a determination is made that the incision output is being made, and then the operation proceeds to step S225.

To determine whether the output is the coagulation output or the incision output, whether the established conduction is the conduction between the electrodes 62a and 62b or that between the electrodes 64a and 64b is determined. The determination can be made by the operation of the holding-force-signal detection circuit 78 to monitor the difference in the resistance value of the resistance R. Thus, a state of holding can be detected.

In step S224 a determination is made that coagulation output is being made. Thus, display of the coagulation is performed on the panel display portion 82. Then, the coagulation waveform is instructed to the waveform forming circuit 80. In step S225 a determination is made that an incision output is being made. Thus, display of the incision is performed on the panel display portion 82. Then, the incision waveform is instructed to the waveform forming circuit 80. After steps S224 and S225 have been performed, the operation proceeds to step S226 so that high-frequency output is performed.

In step S227 a state of the foot switch 86 is determined. The foregoing steps S223 to S227 are repeated until the foot switch 86 is switched off.

If the foot switch 86 is switched off in step S227, the operation proceeds to step S228 so that all of the high-frequency output, display of the output, display of the coagulation and display of the incision are interrupted.

Figure 23:
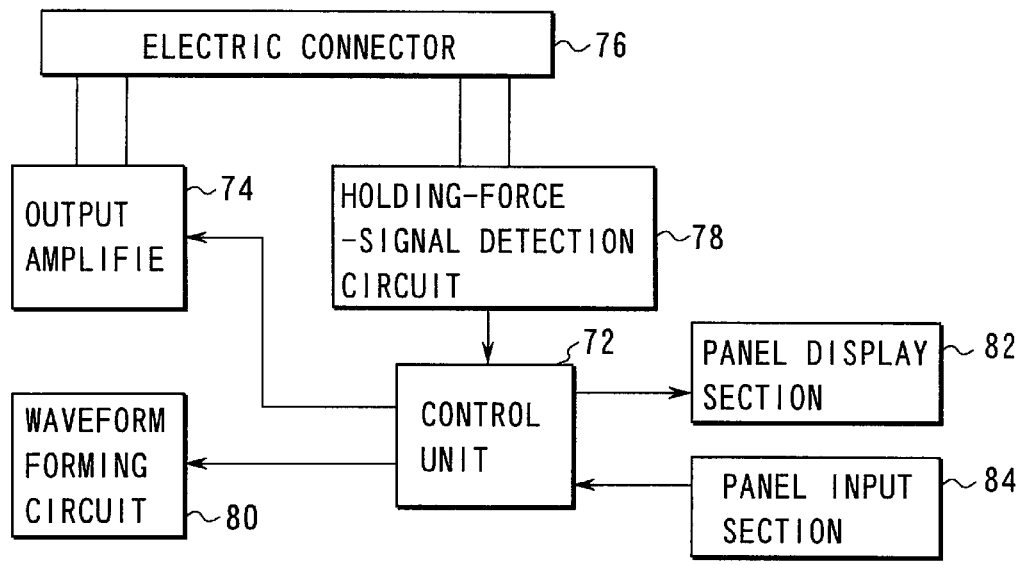
FIG. 23 is a block diagram showing the electrical structure of a portion including an electric knife body according to a fifteenth embodiment of the present invention.
Figure 24:
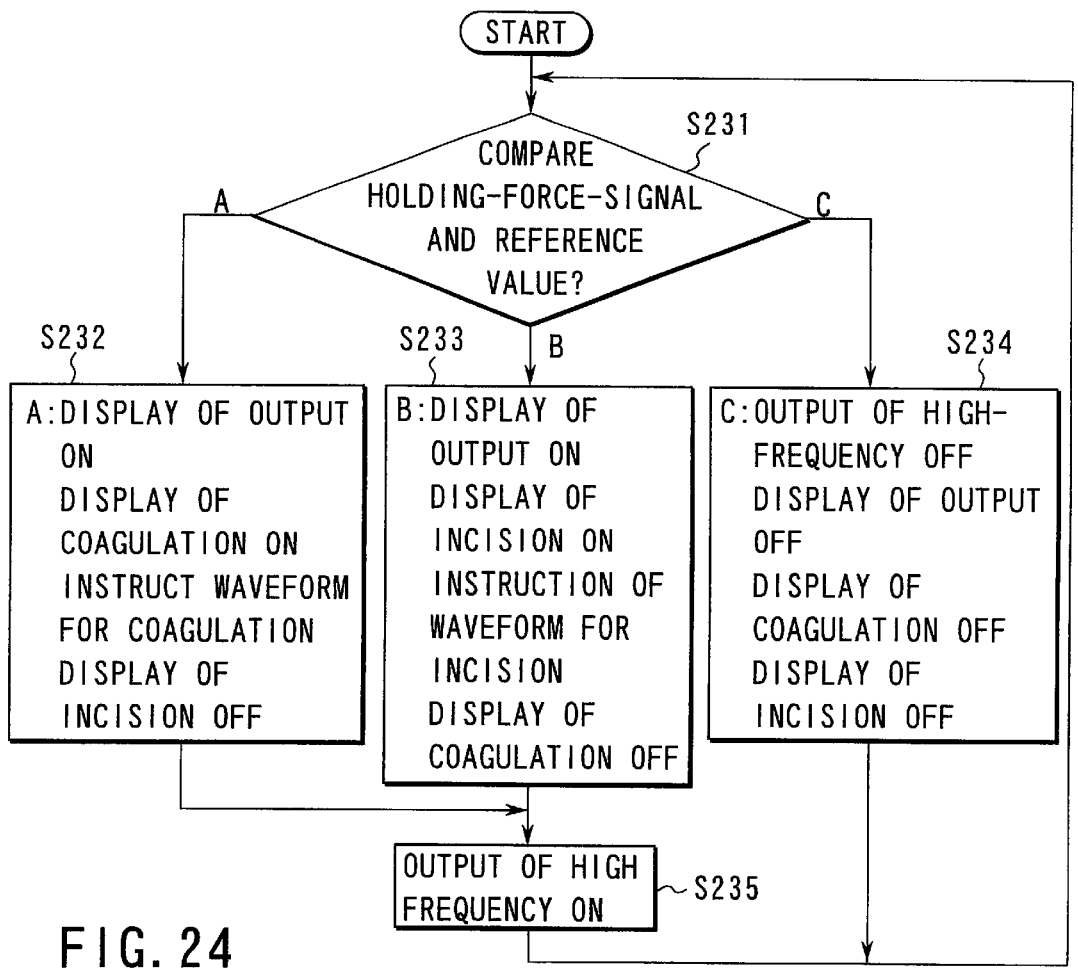
FIG. 24 is a flow chart showing the operation of the fifteenth embodiment of the present invention.

Referring to FIGS. 23 and 24, a fifteenth embodiment of the present invention will now be described.

FIG. 23 is a block diagram showing the electrical structure of a portion including an electric knife body according to the fifteenth embodiment.

The structure according to this embodiment is different from the structure shown in FIG. 21 in that the foot switch is not required. The other structures are the same as those according to the fourteenth embodiment shown in FIG. 21. Therefore, the same elements are given the same reference numeral and omitted from description.

Referring to a flow chart shown in FIG. 24, the operation of the fifteenth embodiment will now be described.

In step S231 the holding-force signal and a predetermined reference value are subjected to a comparison. Two reference values are employed in this embodiment so as to be compared with the holding-force signal. Therefore, results of the comparisons with the two reference values are classified into three results composed of A, B and C.

That is, when determination result A has been made, the operation proceeds to step S232 so that the output for coagulation is selected. If determination result B is made, the operation proceeds to step S233 so that the output for the incision is selected. If the output for the coagulation and the output for the incision are selected, the operation proceeds to step S235 so that the output of high frequency is performed.

If determination result C is made in step S231, the operation proceeds to step S234 so that all of outputs for the curing operation are interrupted.

The fourteenth and fifteenth embodiments may be modified as follows.

That is, the holding-force signal which is transmitted from the bipolar cutting forceps may be a discrete value (for example, a digital value) in place of the foregoing analog value.

A modification may be employed in which either of two types of signals is transmitted to the power source so that coagulation and incision are switched.

Another modification may be employed in which any one of three types of signals is transmitted.

Figure 25:
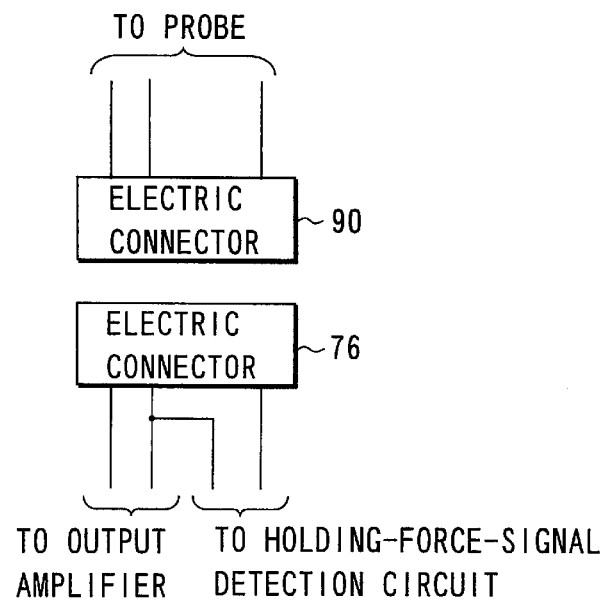
FIG. 25 is a block diagram showing a sixteenth embodiment such that only a portion is illustrated in which a connection cable of a bipolar cutting forceps of an electric medical apparatus and an electric knife body are connected to each other.

Referring to FIG. 25, a sixteenth embodiment of the present invention will now be described.

FIG. 25 is a block diagram showing only a portion in which a connection cable for the bipolar cutting forceps of an electric medical apparatus according to this embodiment and an electric knife body are connected to each other. The other structures are similar to those according to the fourteenth embodiment. Therefore, the similar structures are omitted from description.

Referring to FIG. 25, one of lines for the holding-force signal and output lines for the curing operation connected to the electric connector 76 is used commonly. As a result, the number of the connection cables for the bipolar cutting forceps which are connected to the electric connector 76 and the number of lines which are connected to a connection cable 76 are made to be three.

Figure 26:
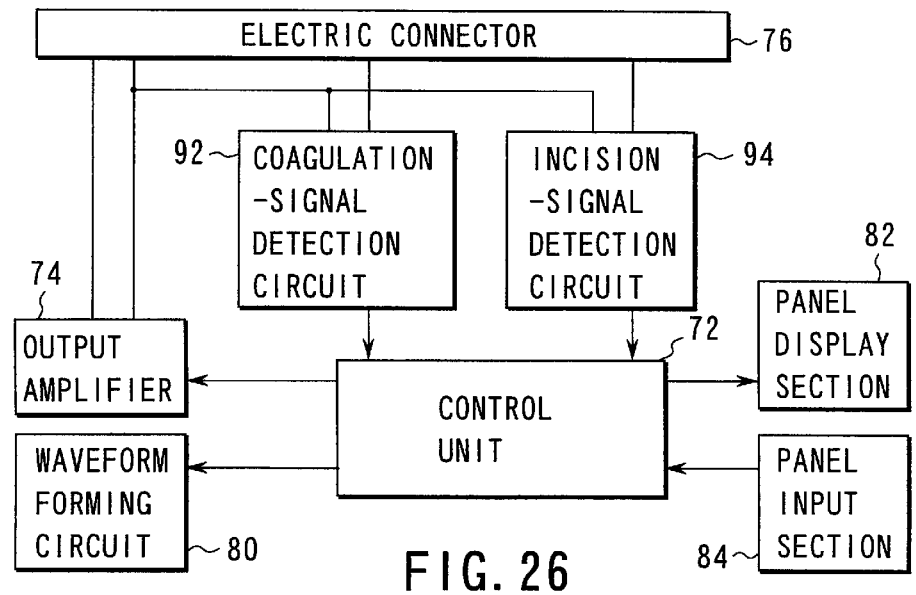
FIG. 26 is a block diagram showing the electrical structure of a portion including an electric knife body according to a seventeenth embodiment of the present invention.
Figure 27:
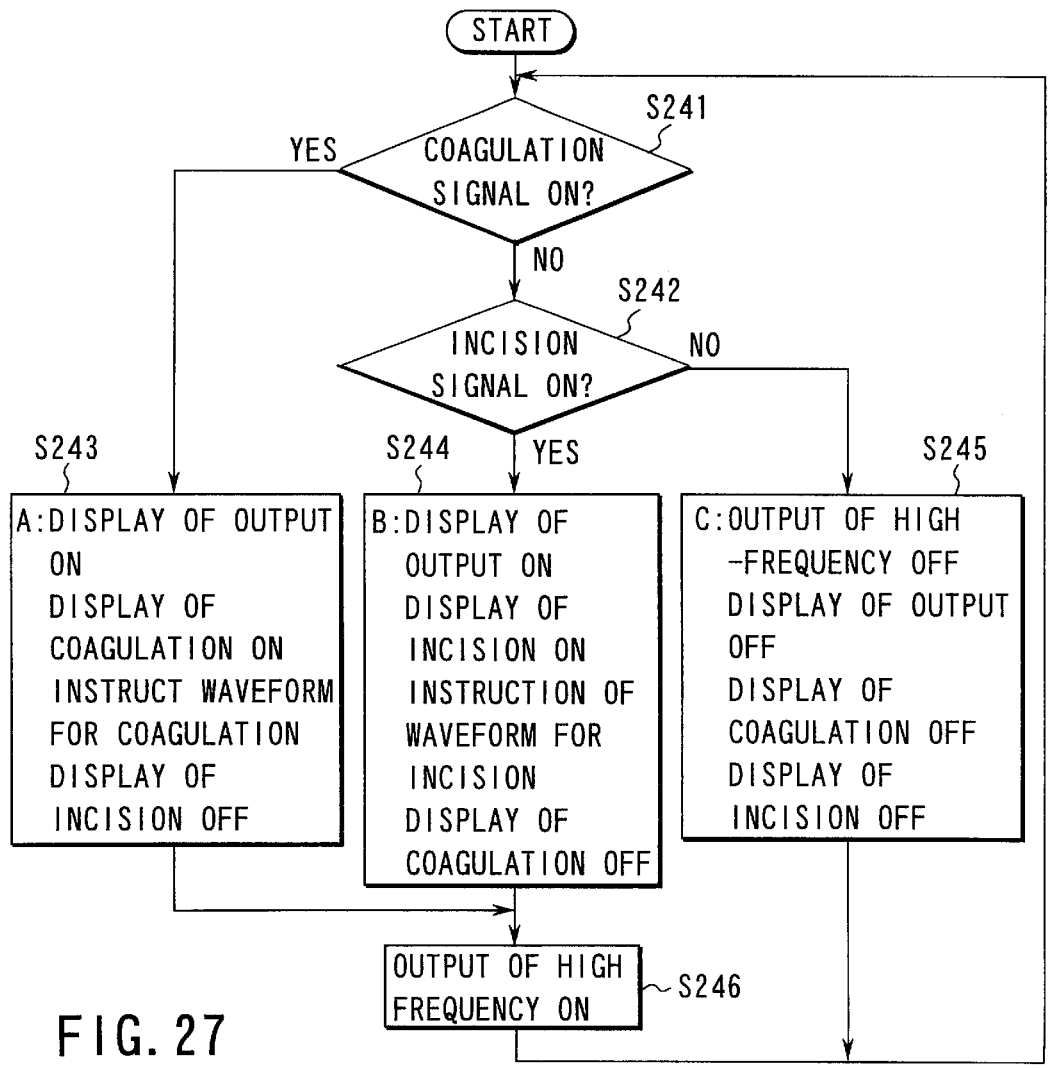
FIG. 27 is a flow chart showing the operation of the seventeenth embodiment of the present invention.

Referring to FIGS. 26 and 27, a seventeenth embodiment of the present invention will now be described.

FIG. 26 is a block diagram showing the electrical structure of a portion including an electric knife body according to the seventeenth embodiment.

The structure according to this embodiment is different from the structure shown in FIG. 21 in that the foot switch and the holding-force-signal detection circuit are omitted. Moreover, a coagulation-signal detection circuit 92 and an incision-signal detection circuit 94 are connected between the control unit 72 and the electric connector 76. In this embodiment, a coagulation signal and an incision signal are individually transmitted from the bipolar cutting forceps.

The other structures are the same as those according to the fourteenth embodiment shown in FIG. 21. Therefore, the same elements are given the same reference numerals and omitted from description.

Referring to a flow chart shown in FIG. 27, the operation of the seventeenth embodiment will now be described.

In step S241 whether or not the coagulation signal has been transmitted is determined. If the coagulation signal is transmitted, the operation proceeds to step S243 so that the output for coagulation is selected.

If the coagulation signal is not transmitted in step S241, whether or not an incision signal has been transmitted is determined in step S242. If the incision signal is transmitted, the operation proceeds to step S244 so that the output for the incision is selected.

If the output for the coagulation or that for the incision is selected in step S243 or step S244, the operation proceeds to step S246 so that the output of high frequency is selected.

If both of the output for the coagulation and that for the incision are not selected in steps S241 and S242, the operation proceeds to step S245 so that the output for the curing operation is interrupted.

In the seventeenth embodiment, the coagulation signal is given priority because the coagulation operation is a relatively safe operation as compared with the incision operation.

An eighteenth embodiment of the present invention will now be described.

In the first to seventeenth embodiment, the bipolar cutting forceps is composed of a forceps having two electrodes. In the eighteenth embodiment, a forceps having three electrodes is employed.

Figure 28:
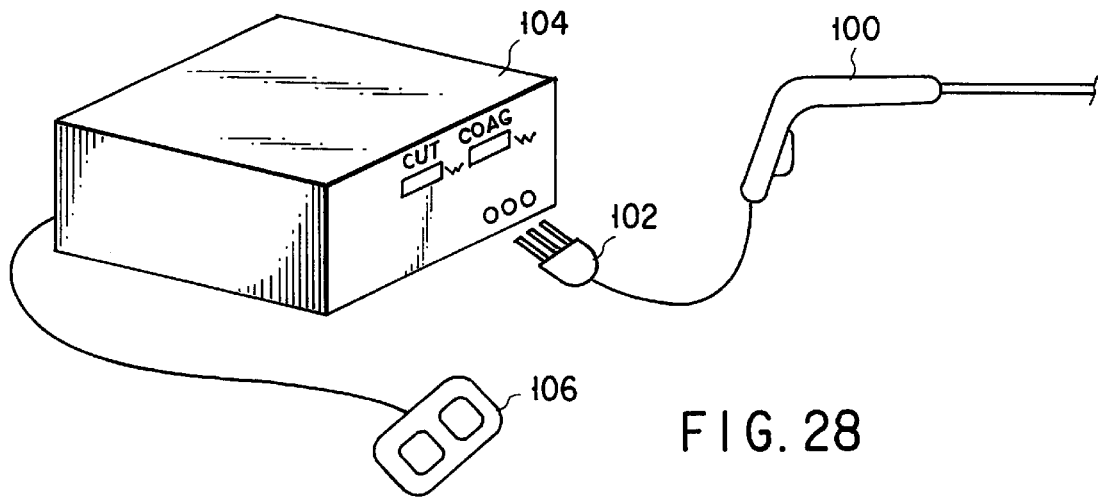
FIG. 28 is a diagram showing an eighteenth embodiment of the present invention such that an example of the structure of an electric medical apparatus is illustrated.

FIG. 28 is a diagram showing an example of the structure of an electric medical apparatus according to this embodiment. A bipolar cutting forceps 100 is, by an electric connector 102, connected to an electric knife body 104 through a connection cable and an electric connector 102. A foot switch 106 is connected to the electric knife body 104.

Figure 29A:
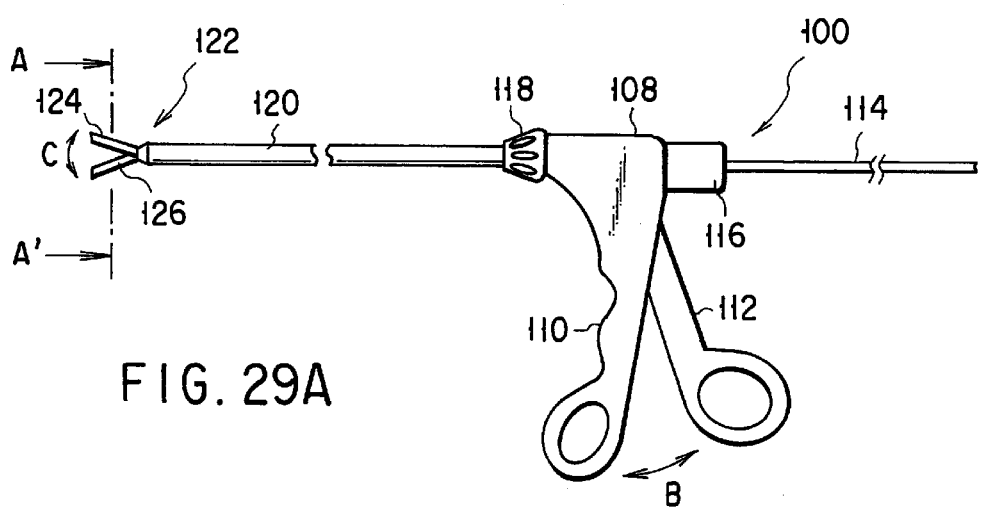
FIG. 29A is a schematic view showing the structure of a bipolar cutting forceps according to the eighteenth embodiment and FIG. 29B is a cross sectional view taken along line A–A' shown in FIG. 29A and showing a processing portion 122.

FIG. 29A is a schematic view showing the structure of the bipolar cutting forceps according to the eighteenth embodiment.

The bipolar cutting forceps 100 has an operating portion 108 which incorporates a stationary handle 110, a movable handle 112 which is able to rotate in a direction indicated by an arrow B in the drawing, a connector receiver 116 to which a cable 114 extending from the electric knife body 104 is connected and a rotative operating portion 118. A sheath 120 serving as an insertion portion which is inserted into the body cavity of a patient is connected to the base portion of the rotative operating portion 118. A treatment portion 122 for holding the living tissue to coagulate or excise the same is disposed at the leading end of the sheath 120. The sheath 120 is rotated into a predetermined direction when the rotative operating portion 118 adjacent to the operating portion 108 is rotated.

The treatment portion 122 incorporates a pair of a first jaw 124 and a second jaw 126. The first and second jaws 124 and 126 are opened/closed when the movable handle 112 of the operating portion 108 is rotated in a direction indicated by an arrow B shown in the drawing. A conductive portion serving as a passage for a high-frequency electric current is electrically connected to the first and second jaws 124 and 126. The conductive member is inserted into the sheath 120 to be extended so as to be connected to the connector receiver 116 provided for the operating portion 108.

Figure 29B:
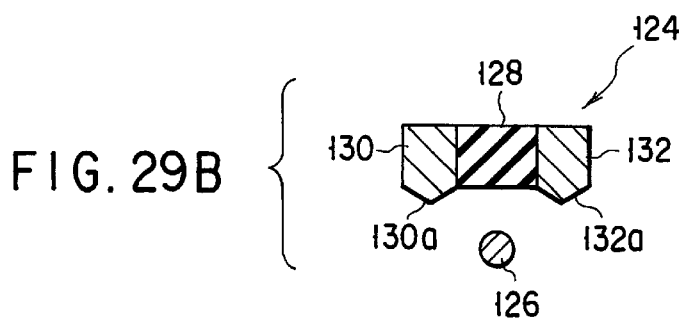

FIG. 29B is a cross sectional view taken along line A–A' shown in FIG. 29A and showing the treatment portion 122.

As described above, the treatment portion 122 incorporates the first and second jaws 124 and 126. The first jaw 124 incorporates two electrode portions 130 and 132 electrically insulated from each other by an insulating member 128 and arranged to perform the coagulation operation. In this embodiment, the electrode portions 130 and 132 for the coagulation operation are disposed on the two sides of the insulating member 128 to hold the insulating member 128 by the electrode portions 130 and 132. The leading ends of the electrode portions 130 and 132 for the coagulation operation are formed into holding portions 130a and 132a formed into sawtooth.

The second jaw 126 is constituted by a rod having a circular cross sectional shape and made of a conductive material so as to serve as an electrode portion for performing the incising operation. The second jaw (the electrode portion) 126 is brought into contact with only the insulating member 128 when the treatment portion 122 has been closed.

With the above-mentioned structure, when the output switch for the incising operation is depressed in a state in which the electric connector 102 has connected the three-electrode forceps to the electric knife body 104, the following switching operation is performed. If the output switch for the coagulation operation is depressed or if a two-electrode forceps is connected, the following switching operation is not performed.

Figure 30:
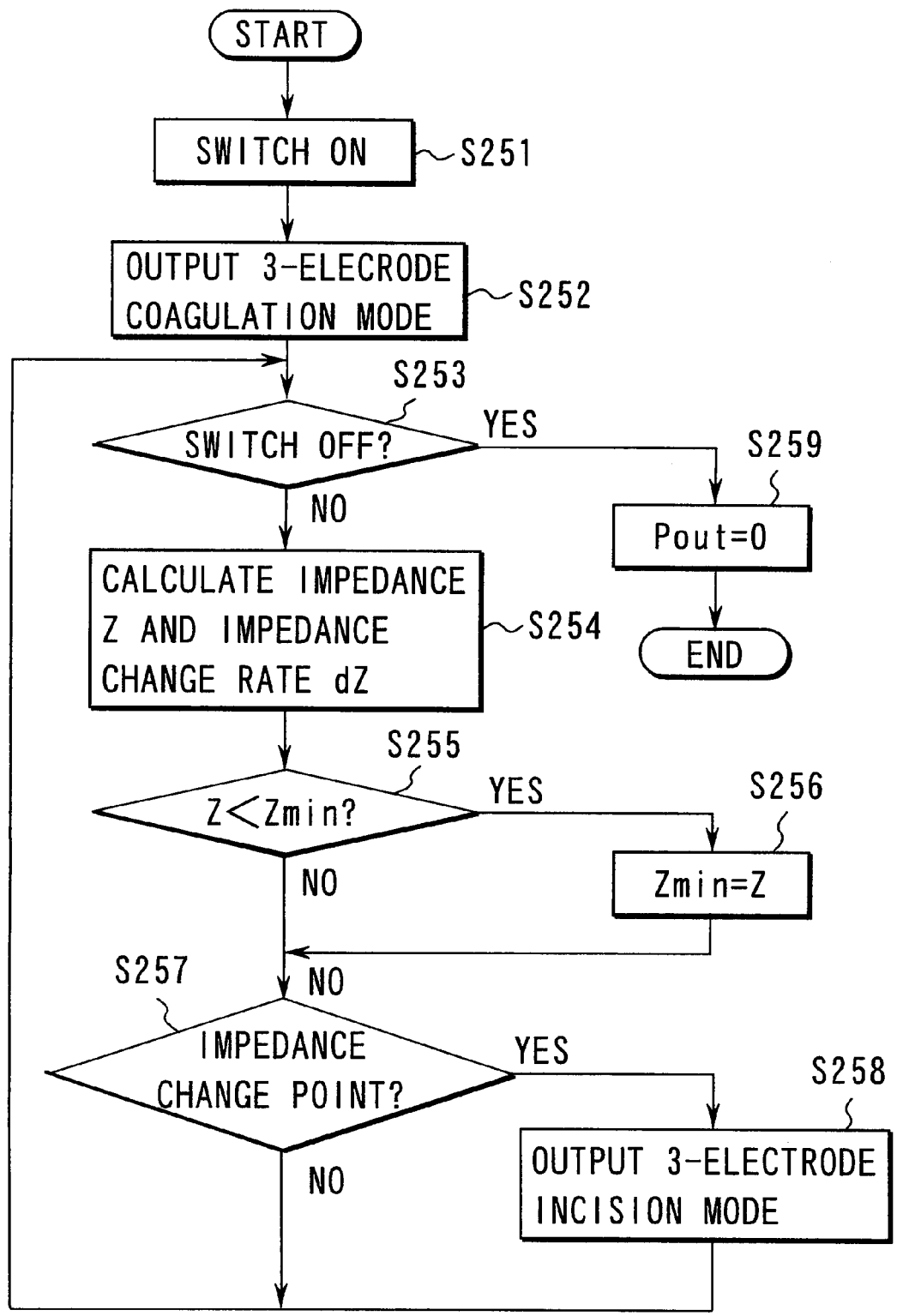
FIG. 30 is a flow chart showing the operation of the eighteenth embodiment of the present invention.

Referring to a flow chart shown in FIG. 30, the operation of the eighteenth embodiment will now be described.

When a hand switch or a foot switch (not shown) is switched on in step S251, output is started in a coagulation mode using the three electrodes. In step S253 a state of the output switch is determined. If the switch is switched on, the operation proceeds to step S254 so that measured values are acquired from voltage and current measuring portions (not shown). Thus, the impedance Z and the impedance change rate dZ are calculated.

In step S255 the calculated impedance Z is compared with the minimum value Zmin. If the impedance is the minimum value, the operation proceeds to step S256 so that the impedance is stored as Zmin. If the impedance Z is not smaller than the minimum value Zmin, the operation proceeds to step S257.

In step S257 whether or not a point of change in the impedance has been detected is determined. If the point of change is not detected, the operation is returned to step S253. If the point of change is detected in step S257, the operation proceeds to step S258 so that switching is performed to put the incising mode using the three electrodes. Then, the operation is returned to step S253.

If a determination is made at an arbitrary moment of time in step S253 that the switch has been switched off, the operation proceeds to step S259 so that output is interrupted.

As for the detection of the point of change in the impedance performed in step S257, a determination can be made that the point of change has been detected if the following conditions are satisfied:

(i) When the impedance change rate dZ is not smaller than the predetermined value dZ1;
(ii) When the impedance Z is not smaller than the upper limit Zlim;
(iii) When the impedance change rate dZ is not smaller than the predetermined value dZ1 or when the impedance Z is not smaller than the upper limit Zlim;

(iv) When the impedance change rate dZ is not smaller than the predetermined value dZ1 and the impedance Z is three or more times the minimum value Zmin; or (v) When (ii) or (iv) is satisfied.

In the eighteenth embodiment, the third electrode is disposed on the inside of the usual two-electrode terminals to be capable or receiving a two-electrode terminal. The third electrode has a switch which is operated when a contact has been inserted. As a result, whether or not the connected forceps is a three-electrode forceps can be determined.

Figure 31:
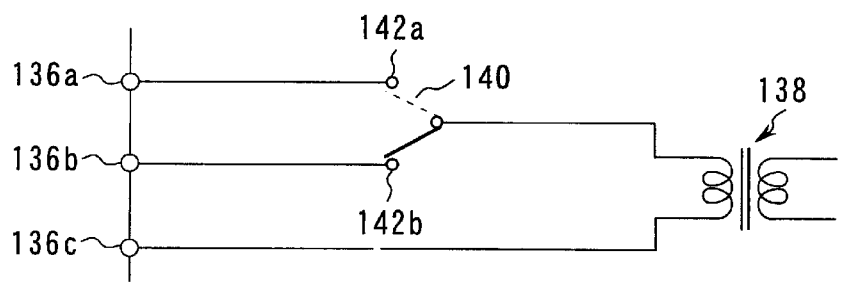
FIG. 31 is a circuit diagram showing an example of the structure of an output switch.

FIG. 31 is a circuit diagram showing an example of the structure of the output switch portion.

As shown in FIG. 31, a switch 140 having terminals 142a and 142b is connected between the three terminals 136a, 136b and 136c and an output transformer 138.

When the medical apparatus is set in the coagulation mode using the three electrodes, the voltage limiter level Vlim is set at 60V and the frequency is set at 500 kHz. Thus, the switch 140 is switched to the terminal 142a. As a result, the output is supplied between the terminals 136a and 136c. Note that an output set to the coagulation operation is performed.

When the medical apparatus is set in the incision mode using the three electrodes, the voltage limiter level Vlim is set at 200V and the frequency is set at 500 kHz. Thus, the switch 140 is switched to the terminal 142b. As a result, the output is supplied between the terminals 136b and 136c. Note that an output set to the incising operation is performed.

When the medical apparatus is set in the coagulation mode and two electrodes are used, the switch 140 is switched to the terminal 142a. Thus, the output is supplied between the terminals 136a and 136c.

As described above, the coagulation operation can be performed with the combination of the electrodes and the output suitable to the coagulation operation. Then, completion of coagulation can be detected to automatically perform the incising operation with the combination with the electrodes and the output suitable to the incising operation. Thus, an undesirable incising operation is not performed in a state where coagulation is in an insufficient state. Thus, a safety operation can be performed. Since the electrodes suitable to the incising operation or those suitable to the coagulation operation can be selected to perform the treatment, time can be shortened. Moreover, excessive burning can be prevented.

A nineteenth embodiment of the present invention will now be described.

The basic structure and operation of the nineteenth embodiment are similar to those according to the eighteenth embodiment. Therefore, a reference to FIGS. 28 and 30 is made and the description is omitted here. The nineteenth embodiment is different from the eighteenth embodiment in that the output switch portion and the output transformer perform switching operations to perform switching between the coagulation and incision using three electrodes.

Figure 32:
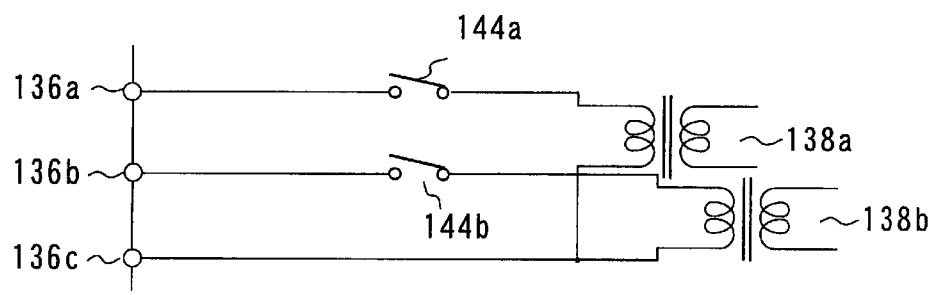
FIG. 32 is a diagram showing a nineteenth embodiment of the present invention such that an example of the structure of an output switch is illustrated.

As shown in FIG. 32, an output transformer 138a is connected between the terminals 136a and 136c through a switch 144a. Similarly, an output transformer 138b is connected between the terminals 136b and 136c through a switch 144b.

When the medical apparatus is set in the coagulation mode using three electrodes, the output transformer 138a is operated. Moreover, the voltage limiter level Vlim is set at 60V and the frequency is set to be 500 kHz. Then, the switch 144a is switched on and the switch 144b is switched off. Thus, the output is supplied between the terminals 136a and 136c. Note that the value of the output is a value set to the coagulating operation.

When the medical apparatus is set in the incising mode using three electrode, the output transformer 138b is operated. Moreover, the voltage limiter level Vlim is set at 200V and the frequency is set to be 350 kHz. Then, the switch 144a is switched off and the switch 144b is switched on. Thus, the output is supplied between the terminals 136b and 136c. Note that the value of the output is a value set to the incising operation.

When the medical apparatus is set in the coagulating operation and two electrodes are used, the output transformer 138a is operated. Moreover, the switch 144a is switched on and the switch 144b is switched off. Thus, the output is supplied between the terminals 136a and 136c.

As described above, according to the nineteenth embodiment, an effect similar to that obtainable from the eighteenth embodiment can be obtained. Moreover, the frequency can be changed.

A twentieth embodiment of the present invention will now be described.

The basic structure and operation of the twentieth embodiment are similar to those according to the eighteenth embodiment. Therefore, a reference to FIGS. 28 to 30 is made and the description is omitted here. The twentieth embodiment is different from the eighteenth embodiment in the combination of output terminals in the output switch portion.

Figure 33:
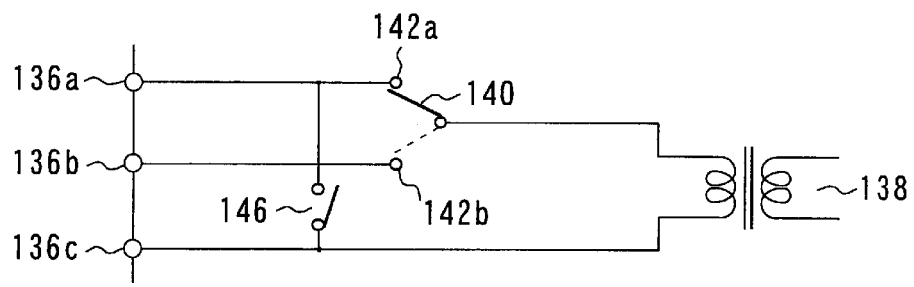
FIG. 33 is a circuit diagram showing a twentieth embodiment of the present invention such that an example of the structure of an output switch is illustrated.

That is, as shown in FIG. 33, a switch 140 having terminals 142a and 142b as shown in the drawing is connected between the three terminals 136a, 136b and 136c and the output transformer 138. Moreover, a switch 146 is connected between the terminals 136a and 136c.

When the medical apparatus is set in the coagulation mode using the three electrodes, the voltage limiter level Vlim is set at 60V and the frequency is set to be 500 kHz. Moreover, the switch 140 is switched to the terminal 142a and the switch 146 is switched off. Thus, the output is supplied between the terminals 136a and 136c. Note that the value of the output is a value set to the coagulating operation.

When the medical apparatus is set in the incising mode using the three electrodes, the voltage limiter level Vlim is set at 200V and the frequency is set to be 500 kHz. Thus, the output is supplied between the terminal 136b and the terminals 136a and 136c. Note that the value of the output is a value set to the incising operation.

When the medical apparatus is set in the coagulation mode and the two electrodes are used, the switch 140 is switched to the terminal 142a and the switch 146 is switched off. Thus, the output is supplied between the terminals 136a and 136c.

As described above, according to the twentieth embodiment, an effect similar to that obtainable from the eighteenths embodiment can be obtained.

A twentieth embodiment of the present invention will now be described.

The basic structure and operation of the twenty-first embodiment are similar to those according to the eighteenth embodiment. Therefore, a reference to FIGS. 28 to 30 is made and the description is omitted here. The twentieth embodiment is different from the eighteenth embodiment in the combination of output terminals in the output switch portion.

Figure 34:
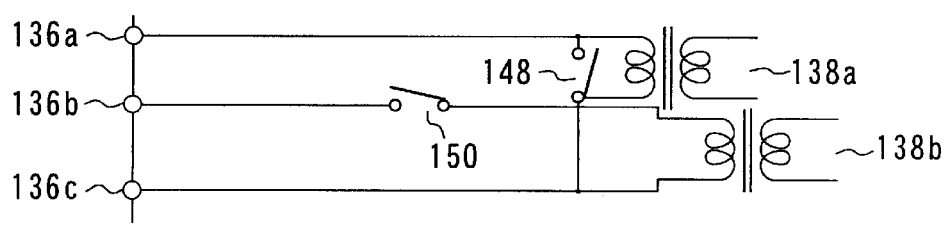
FIG. 34 is a circuit diagram showing a twenty-first embodiment of the present invention such that an example of the structure of an output switch is illustrated.

That is, as shown in FIG. 34, a switch 148 and the output transformer 138a are connected between the terminals 136a and 136c. Moreover, the output transformer 138b is connected between the terminals 136b and 136c through a switch 150.

When the medical apparatus is set in the coagulation mode using the three electrode, the output transformer 138a is operated. Moreover, the voltage limiter level Vlim is set at 60V and the frequency is set to be 500 kHz. Then, both of the switches 148 and 150 are switched off. Thus, the output is supplied between the terminals 136a and 136c. Note that the value of the output is a value set to the coagulation operation.

When the medical apparatus is set in the incision mode using the three electrodes, the output transformer 138b is operated. Moreover, the voltage limiter level Vlim is set at 200V and the frequency is set to be 350 kHz. The switch 140 is switched to the terminal 142b and the switch 146 is switched on. Thus, the output is supplied between the terminal 136b and the terminals 136a and 136c. Note that the value of the output is a value set to the incising operation.

When the medical apparatus is set in the coagulation mode using the two electrodes, an output transformer 76a is operated. Moreover, both of switches 81 and 82 are switched off. Thus, the output is supplied between terminals 75a and 75c.

According to the twenty-first embodiment, an effect similar to that obtainable from the eighteenth embodiment can be obtained.

Note that the third electrode detection portion according to the eighteenth to twenty-first embodiments may be structured as shown in FIG. 35.

In a state as shown in FIG. 35A in which a connection pin 158 is not inserted into a connector receiver 156, a detection switch 160 comprising contact members 160a and 160b is disposed in a portion of the connector receiver 156, that is, in the upper portion in this embodiment. In the foregoing state, the contact member 160a and the contact member 160b are not in contact with each other. Thus, a fact is meant that the connection pin 158 has not been detected.

When the connection pin 158 has been inserted into the connector receiver 156 as shown in FIG. 35B, the contact member 160a is upwards moved by the connection pin 158. Thus, the contact member 160a is brought into contact with the contact member 160b. Thus, the detection switch 160 is switched on so that existence of a third electrode is detected.

A twenty-second embodiment of the present invention will now be described.

In the twenty-second embodiment, the three-electrode forceps is detected in accordance with conduction of electrodes established when the connection pin has been inserted.

That is, as shown in FIG. 36, electrodes 162a and 162b are disposed in a portion of the inner wall of the connector receiver 156. When the connection pin 158 has been inserted into the connector receiver 156, the electrodes 162a and 162b are conducted to each other through the connection pin 158. As a result, existence of the third electrode can be detected.

According to the twenty-second embodiment, the detection can electrically be performed without a necessity of holding the movable portion of the detection switch.

When a living tissue is coagulated and incised by combining the bipolar cutting forceps and the high-frequency oscillator with each other, repetition of the above-mentioned operations sometimes causes the organism to have a high impedance (denaturing takes place owning to heat) only when the organism is held by dint of the previous heat of the jaws. Thus, sufficient energization for the coagulation operation is sometimes inhibited. The reason for this lies in that the usual load characteristic encounters reduction in the output in the high impedance region.

Therefore, a twenty-third embodiment is enabled to sufficiently perform energization required for the coagulation operation of the organism denatured with heat.

Referring to FIGS. 37 to 41, the structure of the twenty-third embodiment of the present invention will now be described. The twenty-third embodiment is structured to prevent excess heat of the jaws owning to repetition of the coagulation operations and the incising operations by improving the load characteristic.

FIG. 37 is a diagram schematically showing the structure of an electric medical apparatus according to the twenty-third embodiment. A bipolar cutting forceps 166 is connected to a high-frequency oscillator 170 through a high-frequency cable 168. A foot switch 172 which is the output switch is connected to the high-frequency oscillator 170.

FIG. 38 is a block diagram showing the electrical structure of the electric medical apparatus shown in FIG. 37.

Referring to FIG. 38, the bipolar cutting forceps 166 is connected to an output amplifier 174 in the high-frequency oscillator 170 through a high-frequency cable. An impedance calculating circuit 176 for calculating the impedance during the output and a control unit 178 for comparing and determining an initial impedance and impedance when energization is being performed for performing the coagulating operation are connected to the output amplifier 174. Moreover, the foot switch 172 is connected to the control unit 178.

Figure 39:
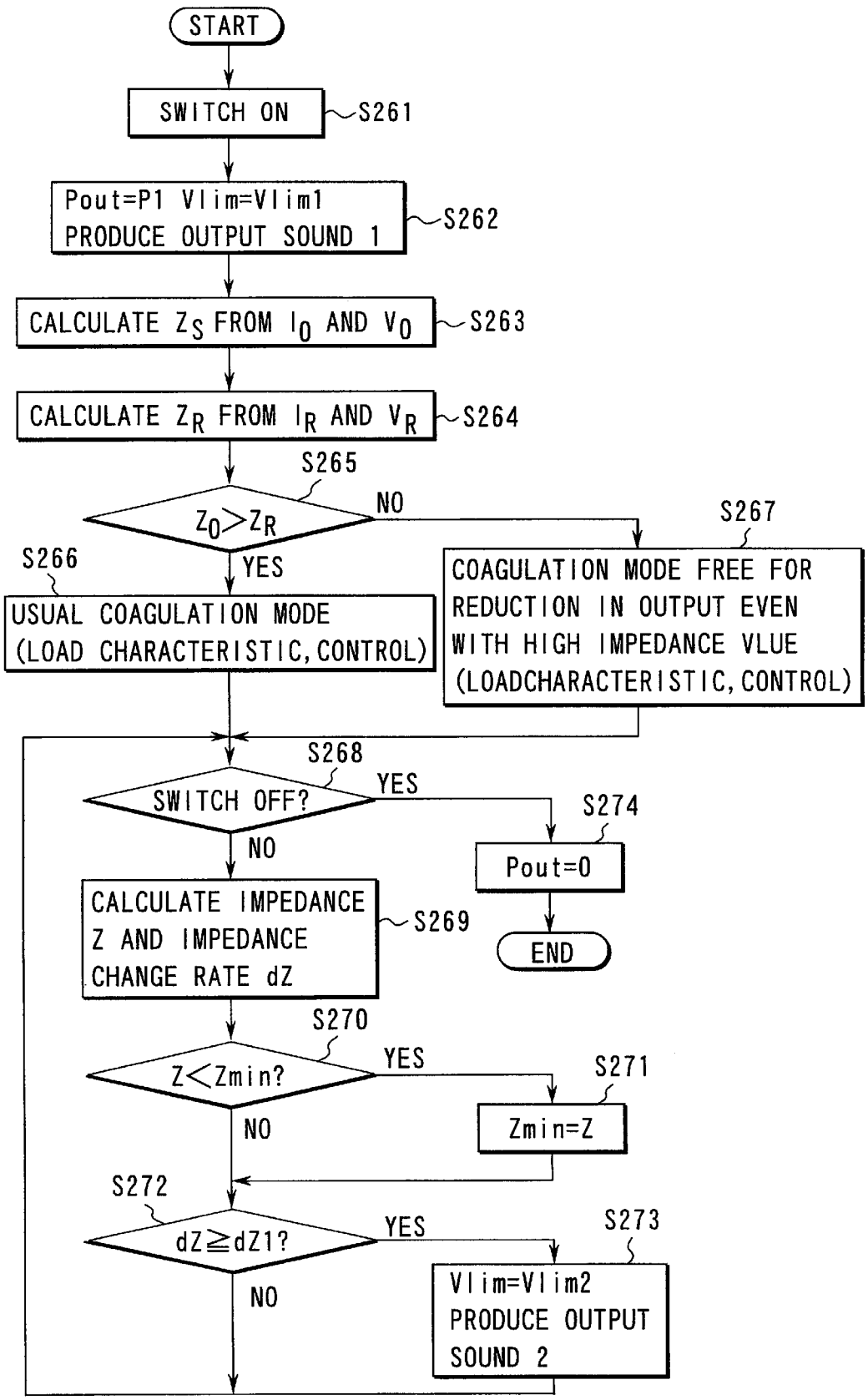
FIG. 39 is a flow chart showing the operation of the twenty-third embodiment of the present invention.

Referring to a flow chart shown in FIG. 39, the operation of the twenty-third embodiment will now be described.

When the foot switch 172 has been switched on in step S261, output is started in step S262 such that the output electric power (Pout) satisfies the relationship P1=40 W and the voltage limiter level (Vlim) satisfies Vlim1=60V. Also output sound 1 is produced. The foregoing output has an output load characteristic suitable to the coagulation of the organism.

In step S263 initial impedance $Z_S$ is calculated by using initial current value $I_0$ and initial voltage level $V_0$ realized when the output has been started. In step S264 impedance $Z_R$ after a predetermined time (0.5 second) has elapsed from start of the energization is calculated by using current value $I_R$ and voltage level $V_R$ realized after a predetermined time has elapsed from the start of the energization, for example, 0.5 second after.

In step S265 the impedance $Z_0$ at the start of the energization and the impedance $Z_R$ after the energization has been started are compared with each other. If the relationship of the two impedance values satisfies $Z_0 \geq Z_R$, a determination is made that the mode is a usual coagulation mode (the load characteristic is controlled). Thus, the operation proceeds to step S266.

FIGS. 40A and 40B show the characteristics when the usual coagulation output is performed in step S266. FIG. 40A is a graph showing change in the impedance, and FIG. 40B shows the load characteristic. As shown in FIG. 40A, the impedance $Z_R$ measured about 0.5 second after is, in the usual coagulation mode, lower than the initial impedance $Z_S$. Moreover, another fact can be understood from the graph shown in FIG. 40B that the output is lowered in a high impedance region.

If the impedance does not satisfy $Z_S \geq Z_R$, a determination is made that the mode is the coagulation mode (the load characteristic is controlled) in which the output is not reduced even with a high impedance. Thus, the operation proceeds to step S267.

FIGS. 41A and 41B show the characteristic in the coagulation mode which is placed in step S267 and in which the output is not reduced even with the high impedance. FIG. 41A is a graph showing change in the impedance, and FIG. 41B is a graph showing the load characteristic. As shown in FIG. 41A, the impedance $Z_R$ measured about 0.5 second after is higher than the initial impedance $Z_S$. As shown in FIG. 41B, reduction in the output is inhibited even in a high impedance region of, for example, about 2 kΩ. Note that a characteristic indicated with a dashed line denotes a usual output for the coagulating operation.

After step S266 or step S267 has been completed, the operation proceeds to step S268 so that a state of the output switch is determined. If the switch has been switched on, the operation proceeds to step S269 so that measured values are acquired from voltage and current sensors (not shown). Then, the impedance Z and the impedance change rate dZ are calculated.

In step S270 the calculated impedance Z is compared with the minimum value Zmin. If the impedance is the minimum value, the operation proceeds to step S271 so that the measured value is stored as Zmin. If the impedance Z is not smaller than the minimum value Zmin, the operation proceeds to step S272.

In step S272 whether or not the impedance change rate dZ is not smaller than a predetermined value dZ1=+300 Ω/sec is determined. If dZ≧dZ1, the operation proceeds to step S273 so that the voltage limiter level Vlim is set such that Vlim2=200V. Moreover, output sound 2 is produced. The output has an output load characteristic suitable to the incising operation. As a result, the incising operation is started.

If the relationship dZ≧dZ is not satisfied in step S272 or if step S273 has been completed, the operation is returned to step S268.

If a determination is made at an arbitrary moment of time in step S268 that the switch has been switched off, the operation proceeds to step S274 so that the output is interrupted.

As described above, according to the twenty-third embodiment, even an organism (an organism having changed impedance) denatured with heat caused from excess heat of the jaws before energization is performed can sufficiently be coagulated because of the energization. Therefore, an area which can be coagulated can be widened.

Referring to FIGS. 42 to 45, a twenty-fourth embodiment of the present invention will now be described.

In the twenty-third embodiment, the load characteristic is improved to overcome denaturing of the living tissue with heat caused from excess heat of the jaws. However, the jaws used in the repetitive coagulating and incising operations are heated, causing a possibility to arise in that burning takes place if the jaws are brought into contact with the organism or the organ of the patient. Therefore, the hot jaws have been cooled by immersing the jaws in physiological salt solution. However, the immersing operation is a complicated operation.

Therefore, the twenty-fourth embodiment is arranged to supply water after the coagulating and incising operations have been performed to cool the hot jaws.

Figure 42:
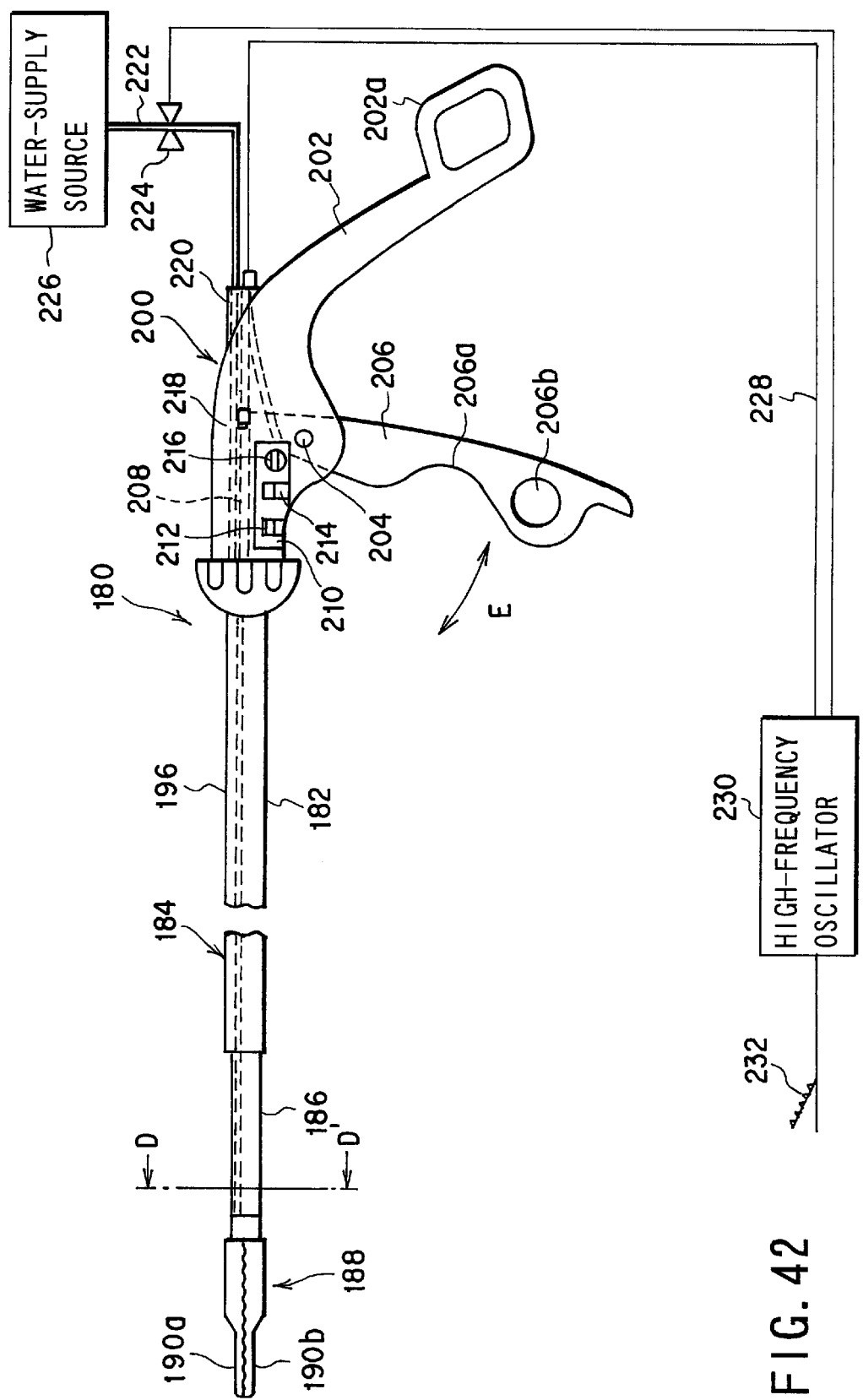
FIG. 42 is a diagram showing the schematic structure of an electric medical apparatus according to a twenty-fourth embodiment of the present invention.
Figure 43A:
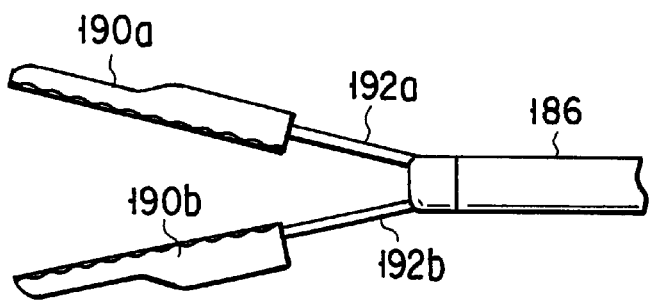
FIG. 43A is a diagram showing the detailed structure of the organization holding portion 188 shown in FIG. 42.

FIG. 42 is a diagram showing the schematic structure of an electric medical apparatus according to the twenty-fourth embodiment. An insertion shaft 184 at the leading end of an external sheath 182 of a bipolar cutting forceps 180 is provided with an organization holding portion 188 through an internal sheath 186. As shown in FIG. 43A, opening/closing jaws 190a and 190b for holding the living tissue are joined to the organization holding portion 188 by jaw-joining springs 192a and 192b.

Figure 43B:
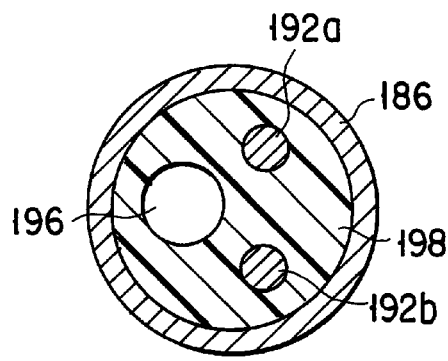
FIG. 43B is a cross sectional view taken along line C–C' shown in FIG. 42

FIG. 43B is a cross sectional view taken along line D–D' shown in FIG. 42 and showing the internal structure of the internal sheath 186. The internal sheath 186 includes a water-supply passage 196 for delivering physiological salt solution supplied from a water-supply source 226 to be described later. Moreover, the internal sheath 186 includes a multi-rumen tube 198 having the jaw-joining springs 192a and 192b.

An operating portion 200 accommodates an internal sheath 208 and a hand switch 210. The hand switch 210 incorporates a coagulation switch 212, an incision switch 214 and a water-supply switch 216.

Moreover, a water-supply channel 218 is formed in the operating portion 200, the water-supply channel 218 being connected to a water-supply tube 222 which is connected to a high-frequency-cable connector 220 disposed in the rear portion of the operating portion 200. The water-supply tube 222 is connected to the water-supply source 226 for delivering physiological salt solution through a water-supply valve 224 for switching water supply on/off.

The high-frequency-cable connector 220 and the water-supply valve 224 of the operating portion 200 are connected to a high-frequency oscillator 230 through a high-frequency cable 228. Moreover, a foot switch 232 which is the output switch is connected to the high-frequency oscillator 230.

Figure 44:
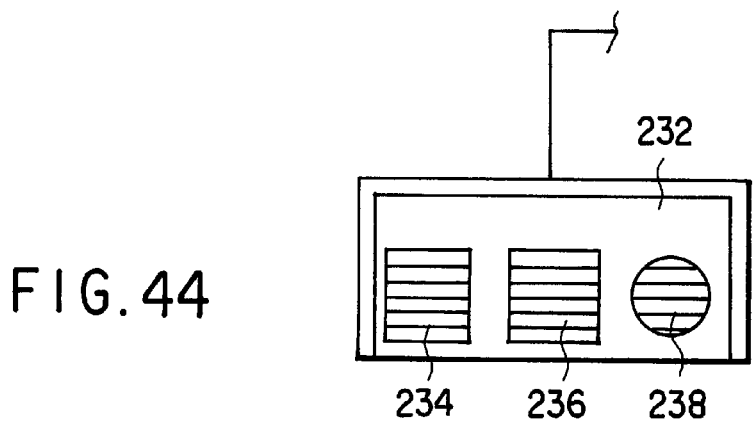
FIG. 44 is a diagram showing an example of the foot switch 232 shown in FIG. 42.

As shown in FIG. 44, and similarly to the hand switch 210, the foot switch 232 is provided with a coagulation switch 234, an incision switch 236 and a water-supply switch 238.

Referring to a flow chart shown in FIG. 45, the operation of the twenty-fourth embodiment having the above-mentioned structure will now be described.

Figure 45:
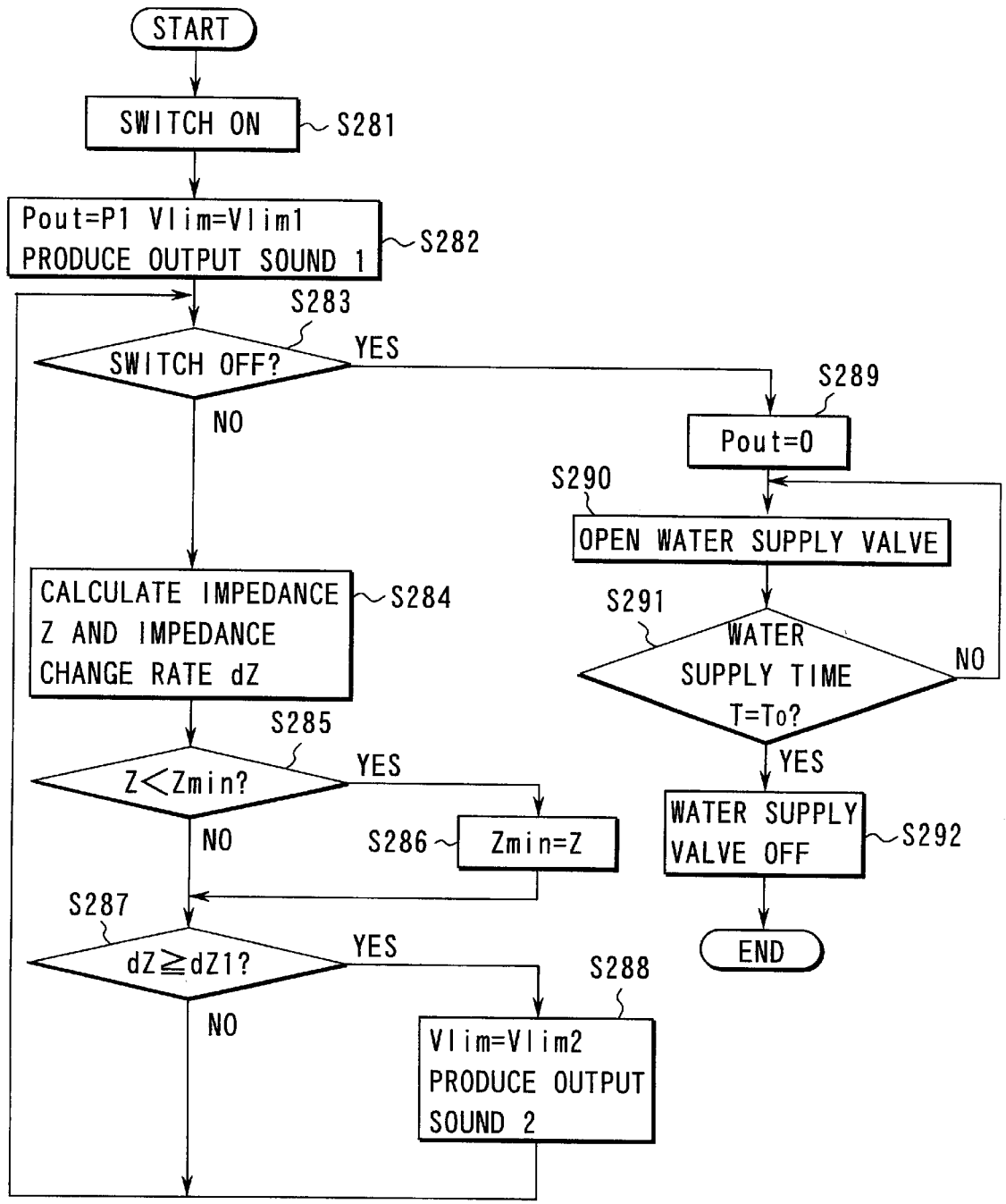
FIG. 45 is a flow chart showing the operation of the twenty-fourth embodiment of the present invention.

In the flow chart shown in FIG. 45, steps S281 to S289 are similar to steps S1 to S9 in the flow chart according to the first embodiment shown in FIG. 4. Therefore, the similar steps are omitted from description.

Figure 43C:
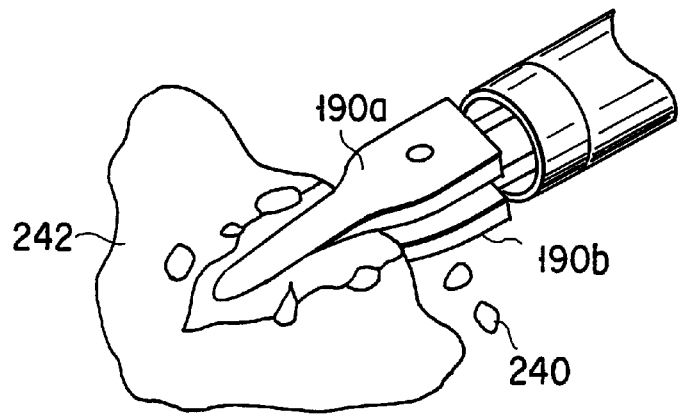
FIG. 43C is a diagram showing a state in which jaws 190a and 190b are cooled with physiological salt solution.

When the output is interrupted in step S289, the water-supply valve 224 is opened in step S290 so that physiological salt solution is supplied from the water-supply source 226. The physiological salt solution 240 supplied from the water-supply source 226 is allowed to pass through the water-supply tube 222, the water-supply channel 218, the water-supply passage 196 and so forth so as to be delivered from a portion between the jaws 190a and 190b, as shown in FIG. 43C. Note that reference numeral 242 represents the living tissue and 240 represents the physiological salt solution which must be delivered.

In step S291 whether or not water supply time T reaches initial set time $T_0$ is determined. Steps S290 and S291 are repeated until the relationship $T=T_0$ is satisfied. If the relationship $T=T_0$ is satisfied, the operation proceeds to step S292 so that the water-supply valve 224 is closed to interrupt supply of the physiological salt solution.

As described above, the hot jaws are heated with supplied water so that denaturing of the organism with heat can be prevented when the organism is held next. Therefore, coagulation can sufficiently be performed. As a result, the coagulating and incising operations can continuously be performed.

Moreover, the risk of burning of the other living tissue and the organ when the coagulating and incising operations are performed can be prevented.

When the water-supply switch 216 joined to the operating portion 200 is switched on/off, the water-supply valve 224 can be opened/closed. Thus, manual supply of water is permitted.

As described above, according to the present invention, an electric medical apparatus can be provided with which the operator is not required to perform another operation between the coagulating operation and the incising operation when the incising operation is performed after the coagulating operation so that the incising operation is automatically performed after the coagulating operation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An electric medical apparatus having a treatment device which is adapted to be brought into contact with a living tissue and which is supplied with high-frequency electric power from a high-frequency power supply unit so as to coagulate or excise the living tissue, said electric medical apparatus comprising:

measuring means for measuring an impedance of the living tissue;

output control means for switching between: (i) a state where said high-frequency electric power has a load characteristic output suitable for coagulating the living tissue, and (ii) a state where said high-frequency electric power has a load characteristic output suitable for excising the living tissue; and control means for, when the high-frequency electric power has the load characteristic output suitable for coagulating the living tissue, detecting completion of coagulation of the living tissue based on a measurement result obtained by said measuring means, and for then automatically controlling said output control means to switch over to the state where the high-frequency electric power has the load characteristic output suitable for excising the living tissue.

2. An electric medical apparatus according to claim 1, wherein said control means detects completion of coagulation of the living tissue when a rate of change in the impedance measured by said measuring means is larger than a predetermined value.

3. An electric medical apparatus according to claim 1, wherein said control means detects completion of coagulation of the living tissue when the impedance measured by said measuring means has a value larger than a predetermined value.

4. An electric medical apparatus according to claim 1, wherein said control means detects completion of coagulation of the living tissue when one of: (i) a rate of change in the impedance measured by said measuring means is larger than a predetermined value, and (ii) the impedance measured by said measuring means has a value larger than a predetermined value.

5. An electric medical apparatus having a treatment device which is adapted to be brought into contact with a living tissue and which is supplied with high-frequency electric power from a high-frequency power supply unit so as to coagulate or excise the living tissue, said electric medical apparatus comprising:

measuring means for measuring an impedance of the living tissue;

output control means for switching between: (i) a state where said high-frequency electric power has a load characteristic output suitable for coagulating the living tissue, and (ii) a state where said high-frequency electric power has a load characteristic output suitable for excising the living tissue;

control means for, when the high-frequency electric power has the load characteristic output suitable for coagulating the living tissue, detecting completion of coagulation of the living tissue when one of: (i) a rate of change in the impedance measured by said measuring means is larger than a predetermined value, and (ii) the impedance measured by said measuring means has a value larger than a predetermined value, and for then automatically controlling said output control means to switch over to the state where the high-frequency electric power has the load characteristic output suitable for excising the living tissue.

* * * * *